(12) United States Patent
Eilers et al.

(10) Patent No.: US 10,485,509 B2
(45) Date of Patent: Nov. 26, 2019

(54) TRACKING SYSTEM FOR AN ULTRASONIC ARC SCANNING APPARATUS

(71) Applicant: ArcScan, Inc., Golden, CO (US)

(72) Inventors: George J. Eilers, Evergreen, CO (US); J. David Stienmier, Denver, CO (US); Wes Weber, Golden, CO (US); John D. Watson, Evergreen, CO (US)

(73) Assignee: ArcScan, Inc., Golden, CO (US)

( * ) Notice: Subject to any disclaimer, the term of this patent is extended or adjusted under 35 U.S.C. 154(b) by 84 days.

(21) Appl. No.: 14/278,960

(22) Filed: May 15, 2014

(65) Prior Publication Data

US 2014/0249422 A1 Sep. 4, 2014

Related U.S. Application Data

(62) Division of application No. 12/347,674, filed on Dec. 31, 2008, now Pat. No. 8,758,252.

(60) Provisional application No. 61/018,606, filed on Jan. 2, 2008, provisional application No. 61/022,449, filed on Jan. 21, 2008, provisional application No. 61/042,141, filed on Apr. 3, 2008, provisional application No. 61/045,447, filed on Apr. 16, 2008.

(51) Int. Cl.
*A61B 8/10* (2006.01)
*A61B 3/10* (2006.01)
*A61B 8/00* (2006.01)

(52) U.S. Cl.
CPC .............. *A61B 8/10* (2013.01); *A61B 3/1005* (2013.01); *A61B 8/4209* (2013.01); *A61B 8/4254* (2013.01); *A61B 8/4263* (2013.01); *A61B 8/4281* (2013.01); *A61B 8/4461* (2013.01)

(58) Field of Classification Search
CPC ....... A61B 3/1005; A61B 8/10; A61B 8/4263; A61B 8/4281; A61B 8/4461; A61B 8/4209; A61B 8/4254
See application file for complete search history.

(56) References Cited

U.S. PATENT DOCUMENTS

| | | | |
|---|---|---|---|
| 3,371,660 A | 3/1968 | Benson | |
| 3,821,891 A | 7/1974 | Collins et al. | |
| 3,997,793 A | 12/1976 | Rogers et al. | |
| 4,092,867 A * | 6/1978 | Matzuk | A61B 8/00 600/445 |

(Continued)

FOREIGN PATENT DOCUMENTS

| | | |
|---|---|---|
| CA | 2295431 | 7/2001 |
| CA | 2299483 | 7/2001 |

(Continued)

OTHER PUBLICATIONS

U.S. Appl. No. 15/048,706, filed Feb. 19, 2016, Levien et al.

(Continued)

*Primary Examiner* — Luther Behringer
(74) *Attorney, Agent, or Firm* — Sheridan Ross, P.C.

(57) ABSTRACT

Embodiments of the present invention are directed to various aspects of imaging systems, including permeable and impermeable barriers separating liquid compartments, one of which contains the object to be imaged and the other an ultrasonic transducer, a fluidic bearing between a transducer carriage and guide supporting the carriage, a linear motor for the carriage, and a location sensing device for the carriage.

20 Claims, 13 Drawing Sheets

(56) References Cited

U.S. PATENT DOCUMENTS

| | | | |
|---|---|---|---|
| 4,114,214 A | 9/1978 | VonHeck | |
| 4,154,114 A | 5/1979 | Katz | |
| 4,183,249 A | 1/1980 | Anderson | |
| 4,206,763 A | 6/1980 | Pedersen | |
| 4,227,780 A | 10/1980 | Ohta et al. | |
| 4,245,250 A | 1/1981 | Tiemann | |
| 4,347,213 A | 8/1982 | Rogers | |
| 4,484,569 A | 11/1984 | Driller et al. | |
| 4,493,877 A | 1/1985 | Burnett | |
| 4,545,385 A | 10/1985 | Pirschel | |
| 4,550,607 A | 11/1985 | Maslak et al. | |
| 4,564,018 A | 1/1986 | Hutchison et al. | |
| 4,807,634 A | 2/1989 | Enjoji et al. | |
| 4,815,047 A | 3/1989 | Hart | |
| 4,817,432 A | 4/1989 | Wallace et al. | |
| 4,823,801 A | 4/1989 | Sakane | |
| 4,858,124 A | 8/1989 | Lizzi et al. | |
| 4,858,613 A | 8/1989 | Fry et al. | |
| 4,930,512 A | 6/1990 | Henriksen et al. | |
| 4,932,414 A | 6/1990 | Coleman et al. | |
| 5,029,587 A | 7/1991 | Baba et al. | |
| 5,079,786 A | 1/1992 | Rojas | |
| 5,103,517 A | 4/1992 | Krouskop | |
| 5,116,114 A | 5/1992 | Nakamura et al. | |
| 5,152,746 A | 10/1992 | Atkinson et al. | |
| 5,293,871 A | 3/1994 | Reinstein et al. | |
| 5,331,962 A | 7/1994 | Coleman et al. | |
| 5,369,454 A | 11/1994 | Reinstein et al. | |
| 5,387,180 A | 2/1995 | Lehmer | |
| 5,460,179 A * | 10/1995 | Okunuki | G10K 11/355 600/444 |
| 5,474,070 A | 12/1995 | Ophir et al. | |
| 5,487,388 A | 1/1996 | Rello et al. | |
| 5,517,991 A | 5/1996 | Herrmann et al. | |
| 5,551,432 A | 9/1996 | Iezzi | |
| 5,556,169 A | 9/1996 | Parrish et al. | |
| 5,614,099 A | 3/1997 | Hirose et al. | |
| 5,626,150 A | 5/1997 | Johnson et al. | |
| 5,626,594 A | 5/1997 | Smith | |
| 5,647,367 A * | 7/1997 | Lum | A61B 8/12 600/463 |
| 5,671,739 A | 9/1997 | Darrow et al. | |
| 5,776,068 A | 7/1998 | Silverman et al. | |
| 5,826,583 A | 10/1998 | Wood | |
| 5,832,550 A | 11/1998 | Hauger et al. | |
| 5,855,207 A | 1/1999 | Moenning et al. | |
| 5,906,205 A | 5/1999 | Hiebert | |
| 5,966,763 A | 10/1999 | Thomas et al. | |
| 5,971,006 A | 10/1999 | Seigerschmidt | |
| 6,053,613 A | 4/2000 | Wei et al. | |
| 6,145,143 A | 11/2000 | Hicks et al. | |
| 6,154,204 A | 11/2000 | Thompson et al. | |
| 6,198,956 B1 | 3/2001 | Dunne | |
| 6,315,727 B1 | 11/2001 | Coleman et al. | |
| 6,318,372 B1 | 11/2001 | Hiebert | |
| 6,334,227 B1 | 1/2002 | Larger | |
| 6,374,439 B2 | 4/2002 | Heimbrock et al. | |
| 6,451,008 B1 | 9/2002 | Frey et al. | |
| 6,460,207 B1 | 10/2002 | Papay et al. | |
| 6,487,447 B1 | 11/2002 | Weimann et al. | |
| 6,491,637 B2 | 12/2002 | Foster et al. | |
| 6,574,813 B2 | 6/2003 | Bolden et al. | |
| 6,629,929 B1 | 10/2003 | Jago et al. | |
| 6,684,433 B2 | 2/2004 | Giori et al. | |
| 6,780,153 B2 * | 8/2004 | Angelsen | A61B 8/00 600/444 |
| 6,837,855 B1 | 1/2005 | Puech | |
| 6,868,569 B2 | 3/2005 | VanSteenburg | |
| 6,887,203 B2 | 5/2005 | Phillips et al. | |
| 6,923,767 B2 | 8/2005 | Saied et al. | |
| 6,981,417 B1 | 1/2006 | Oravecz | |
| 7,048,690 B2 | 5/2006 | Coleman et al. | |
| 7,168,116 B2 | 1/2007 | Reger et al. | |
| 7,237,898 B1 | 7/2007 | Hohla | |
| 7,356,905 B2 | 4/2008 | Ketterling et al. | |
| 7,451,507 B2 | 11/2008 | Brinkerhoff et al. | |
| 7,454,024 B2 | 11/2008 | Ketterling et al. | |
| 7,474,041 B2 | 1/2009 | Ketterling et al. | |
| 7,480,058 B2 | 1/2009 | Zhao et al. | |
| 7,611,507 B2 | 11/2009 | Raksi et al. | |
| 7,708,342 B2 | 5/2010 | Leach | |
| 7,920,909 B2 | 4/2011 | Lyon et al. | |
| 8,064,989 B2 | 11/2011 | Brown et al. | |
| 8,068,647 B2 | 11/2011 | Lin | |
| 8,115,935 B2 | 2/2012 | Everett et al. | |
| 8,317,709 B2 | 11/2012 | Eilers et al. | |
| 8,475,384 B2 * | 7/2013 | Hart | A61B 8/00 600/459 |
| 8,496,588 B2 | 7/2013 | Eilers et al. | |
| 8,510,883 B2 | 8/2013 | Eilers et al. | |
| 8,732,878 B2 | 5/2014 | Eilers et al. | |
| 8,758,252 B2 | 6/2014 | Ellers et al. | |
| 8,824,743 B2 | 9/2014 | Daigle | |
| 2001/0020200 A1 * | 9/2001 | Das | B25J 9/1689 700/260 |
| 2002/0085173 A1 | 7/2002 | Schippert et al. | |
| 2002/0143252 A1 | 10/2002 | Dunne et al. | |
| 2003/0004416 A1 | 1/2003 | Phillips et al. | |
| 2003/0142269 A1 | 7/2003 | Cumming | |
| 2004/0200754 A1 | 10/2004 | Hagemeier | |
| 2004/0220478 A1 | 11/2004 | Wallace et al. | |
| 2005/0067494 A1 * | 3/2005 | Ito | G06K 7/10683 235/454 |
| 2005/0120479 A1 | 6/2005 | Habashi et al. | |
| 2005/0256406 A1 * | 11/2005 | Barthe | A61B 8/14 600/444 |
| 2006/0029525 A1 | 2/2006 | Laugharn, Jr. et al. | |
| 2006/0106313 A1 | 5/2006 | Hobson | |
| 2006/0241533 A1 | 10/2006 | Geller | |
| 2006/0288487 A1 | 12/2006 | Roleder et al. | |
| 2007/0051362 A1 | 3/2007 | Sullivan et al. | |
| 2007/0083995 A1 | 4/2007 | Purdy et al. | |
| 2007/0239020 A1 | 10/2007 | Iinuma et al. | |
| 2007/0239030 A1 | 10/2007 | Prager et al. | |
| 2007/0276233 A1 | 11/2007 | Besson et al. | |
| 2008/0097214 A1 | 4/2008 | Meyers et al. | |
| 2008/0146939 A1 * | 6/2008 | McMorrow | A61B 8/0833 600/462 |
| 2008/0161696 A1 | 7/2008 | Schmitt et al. | |
| 2009/0088623 A1 | 4/2009 | Vortman et al. | |
| 2009/0234369 A1 | 9/2009 | Bax et al. | |
| 2009/0318758 A1 | 12/2009 | Farr et al. | |
| 2010/0004538 A1 | 1/2010 | Eilers et al. | |
| 2010/0031448 A1 | 2/2010 | Hijkema | |
| 2010/0217125 A1 | 8/2010 | Kadokura et al. | |
| 2010/0229306 A1 | 9/2010 | Reeder et al. | |
| 2010/0249562 A1 | 9/2010 | Zhang | |
| 2010/0321697 A1 | 12/2010 | Zheng et al. | |
| 2011/0172511 A1 | 7/2011 | Peterson et al. | |
| 2012/0053459 A1 | 3/2012 | Eilers et al. | |
| 2012/0209118 A1 | 8/2012 | Warnking | |
| 2012/0320368 A1 | 12/2012 | Jiao | |
| 2013/0072755 A1 | 3/2013 | Papania et al. | |
| 2013/0085370 A1 | 4/2013 | Friedman | |
| 2013/0144171 A1 | 6/2013 | Watson | |
| 2013/0237826 A1 | 9/2013 | Levien | |
| 2013/0310692 A1 | 11/2013 | Watson et al. | |
| 2014/0009741 A1 | 1/2014 | Levien et al. | |
| 2014/0371589 A1 | 12/2014 | Nakabayashi | |
| 2015/0031998 A1 | 1/2015 | Kyono et al. | |
| 2015/0238166 A1 | 8/2015 | Heath et al. | |
| 2015/0265243 A1 | 9/2015 | Kelly | |
| 2017/0119345 A1 | 5/2017 | Levien et al. | |

FOREIGN PATENT DOCUMENTS

| | | |
|---|---|---|
| CA | 2395203 | 7/2001 |
| CA | 2409234 | 4/2004 |
| JP | 2006-149001 | 6/2006 |

(56) References Cited

FOREIGN PATENT DOCUMENTS

| JP | 2006149001 | * | 6/2006 |
|---|---|---|---|
| WO | WO 2013/103167 | | 7/2013 |

OTHER PUBLICATIONS

U.S. Appl. No. 15/081,549, filed Mar. 25, 2016, Eilers et al.
Angelson et al. "Which transducer array is best?" European Journal of Ultrasound, 1995, vol. 2., pp. 151-164.
Binder, "SL-OCT and Ultrasound Support the Need for New Phakic IOL Sizing Strategies," Euro Times, Mar. 2007, p. 11.
Coleman et al., "Ultrasonography of the Eye and Orbit," Second Edition, published by Lippincott Williams & Wilkins, 2006, pp. 1-186.
Izatt et al., "Theory of Optical Coherence Tomography," Chap. 2 of "Optical Coherence Tomography Technology and Applications," Drexler and Fujimoto eds, ISBN:978-3-540-77549-2, 2008, pp. 47-72.
Ketterling, "Design and Fabrication of a 40-MHz Annular Array Transducer," IEEE Transactions on Ultrasonics, Ferroelectrics, and Frequency Control, Apr. 2005, vol. 52, No. 4, pp. 672-681.
Ketterling, "Operational Verification of a 40-MHz Annular Array Transducer," IEEE Transactions on Ultrasonics, Ferroelectrics, and Frequency Control, Mar. 2006, vol. 53, No. 3, pp. 623-630.
Mamou, "Chirp-Coded Excitation Imaging With a High-Frequency Ultrasound Annular Array," IEEE Transactions on Ultrasonics, Ferroelectrics, and Frequency Control, Feb. 2008, vol. 55, No. 2, pp. 508-513.
Pinero et al., "Equivalence, Differences Identified in Biometric Analysis," Cataract & Refractive Surgery Today, Mar. 2008, vol. 3, No. 12, pp. 46-49.
Reinstein et al., "Repeatability of Layered Corneal Pachymetry With the Artemis Very High Frequency Digital Ultrasound Arc-Scanner," J. Refractive Surg., vol. 26(9), 2009, original article, 6 pages.
Reinstein, "Subsurface Screening for Keratoconus—Accurate Measurements of the Epithelial and Stromal Layers Aid in Diagnosis," Cataract and Refractive Surgery Today, May 2007, pp. 88-89.
Roholt, "Sizing the Visian ICL," Cataract and Refractive Surgery Today, May 2007, p. 50.
Silverman et al., "Improved System for Sonographic Imaging and Biometry of the Cornea," J. Ultrasound Med., 1997, vol. 16, pp. 117-124.
International Search Report for International Application No. PCT/US2008/088671, dated May 8, 2009, 4 pages.
Written Opinion for International Application No. PCT/US2009/088671, dated May 8, 2009, 5 pages.
International Preliminary Report on Patentability for International Application No. PCT/US2009/088671, dated Jul. 15, 2010, 7 pages.
Extended Search Report for European Patent Application No. 08870422.6, dated May 31, 2011 9 pages.
Official Action for European Patent Application No. 08870422.6, dated Jun. 17, 2011 1 page.
Official Action (with English translation) for Japanese Patent Application No. 2010-541542, dated Aug. 13, 2013, 8 pages.
International Search Report for International Application No. PCT/US2009/039505, dated Jun. 3, 2009.
International Preliminary Report on Patentability for International Application No. PCT/US2009/039505, dated Oct. 14, 2010, 4 pages.
Written Opinion for International Application No. PCT/US2009/039505, dated Jun. 3, 2009, 7 pages.
Official Action for U.S. Appl. No. 12/418,392, dated Aug. 3, 2011 14 pages.
Official Action for U.S. Appl. No. 12/347,674, dated Oct. 27, 2011 9 pages Restriction Requirement.
Official Action for U.S. Appl. No. 12/347,674, dated Mar. 2, 2012 10 pages.
Official Action for U.S. Appl. No. 12/347,674, dated Aug. 14, 2012 10 pages.
Official Action for U.S. Appl. No. 12/347,674, dated Jun. 27, 2013 10 pages.
Notice of Allowance for U.S. Appl. No. 12/347,674, dated Jan. 30, 2014 8 pages.
Official Action for U.S. Appl. No. 12/418,392, dated Feb. 1, 2012 22 pages.
Official Action for U.S. Appl. No. 12/418,392, dated Jun. 29, 2012 20 pages.
Notice of Allowance for U.S. Appl. No. 12/418,392, dated Mar. 13, 2013 20 pages.
"Campbell-Walsh Urology," Tenth Edition, W.B. Saunders, 2012, ISBN 978-1-4160-6911-9, abstract only, 2 pages.
"Information for Manufacturers Seeking Marketing Clearance of Diagnostic Ultrasound Systems and Transducers", 2008, Center for Devices and Radiological Health, 68 pages.
Kim et al., "20 MHz/40 MHz Dual Element Transducers for High Frequency Harmonic Imaging," IEEE Transactions on Ultrasonics, Ferroelectrics and Frequency Control, 2008, vol. 55(12), pp. 2683-2691, 25 pages.
Misaridis et al., "Use of Modulated Excitation Signals in Medical Ultrasound. Part I: Basic Concepts and Expected Benefits," IEEE Transactions on Ultrasonics, Ferroelectrics, and Frequency Control, 2005, vol. 52(2), pp. 177-191.
Sanchez et al., "A Novel Coded Excitation Scheme to Improve Spatial and Contrast Resolution of Quantitative Ultrasound Imaging," IEEE Transactions on Ultrasonics, Ferroelectrics, and Frequency Control, 2009, vol. 56(10), pp. 2111-2123, abstract only, 1 page.
Silverman et al., "High-Frequency Ultrasonic Imaging of the Anterior Segment Using an Annular Array Transducer," Ophthalmology, 2007, vol. 114(4), pp. 816-822, 15 pages.
Song et al., "Coded excitation for ultrasound tissue harmonic imaging," Ultrasonics, received in revised form 18, Dec. 2009, retrieved from journal homepage: www.elsevier.com/locate/ultras, pp. 1-7.

* cited by examiner

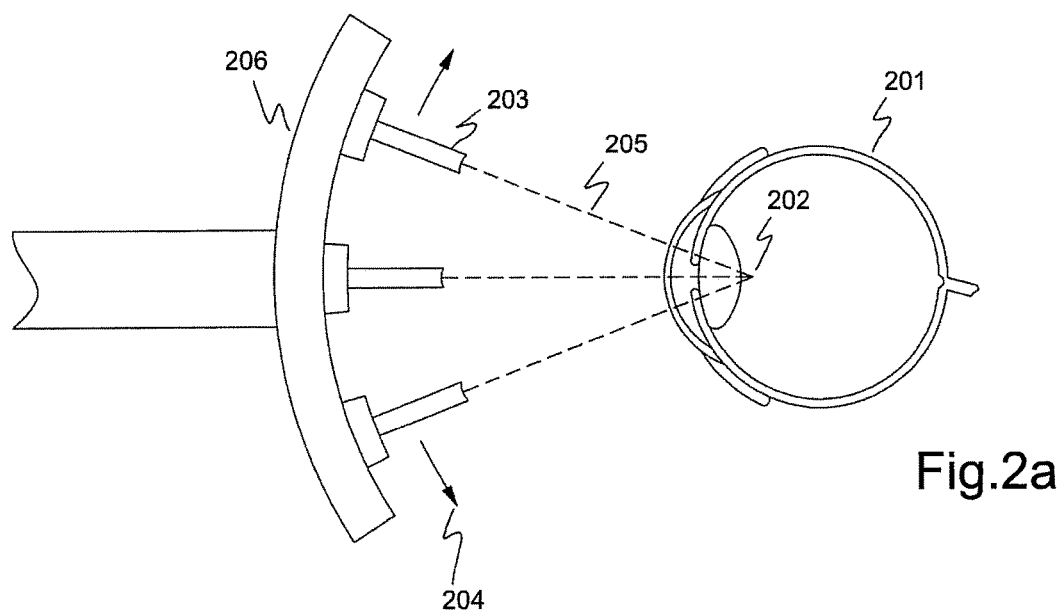
Fig.2a
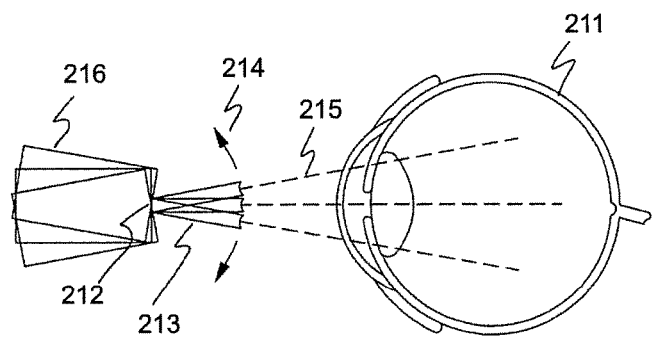
Fig. 2b
Figure 2

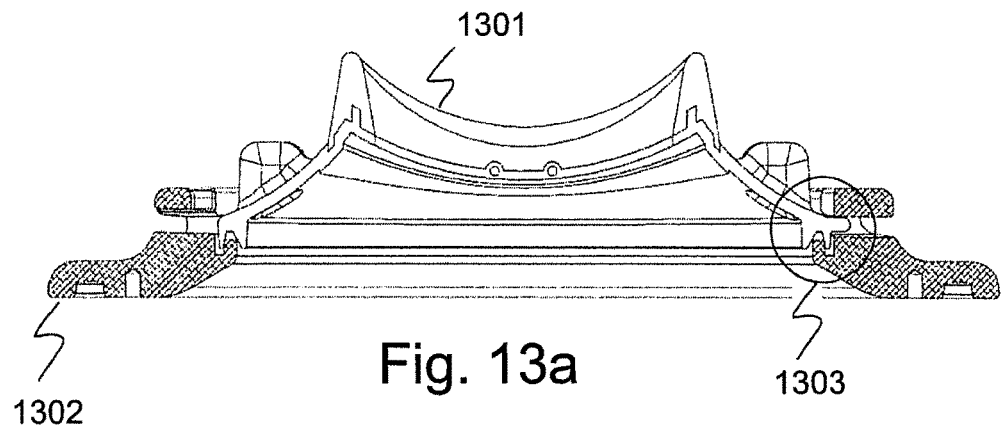
Fig. 13a
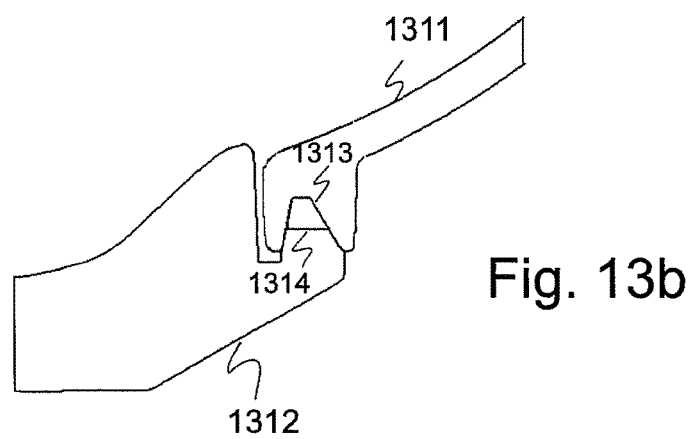
Fig. 13b
Figure 13

TRACKING SYSTEM FOR AN ULTRASONIC ARC SCANNING APPARATUS

CROSS REFERENCE TO RELATED APPLICATIONS

The present application is a divisional of U.S. application Ser. No. 12/347,674, filed Dec. 31, 2008, entitled "Innovative Components for an Ultrasonic Arc Scanning Apparatus", which claims the benefits, under 35 U.S.C. § 119(e), of U.S. Provisional Application Ser. No. 61/018,606 entitled "Innovative Components for an Ultrasonic Arc Scanning Apparatus", filed Jan. 2, 2008; 61/022,449 entitled "Innovative Components for an Ultrasonic Arc Scanning Apparatus", filed Jan. 21, 2008; 61/042,141 entitled "Innovative Components for an Ultrasonic Arc Scanning Apparatus", filed Apr. 3, 2008; and 61/045,447 entitled "Innovative Components for an Ultrasonic Arc Scanning Apparatus", filed Apr. 16, 2008, all of which are incorporated herein by these references.

FIELD

The present invention relates to ultrasonic imaging of biological materials such as the cornea and natural lens of the eye and in particular relates to components, such as a scan head, transducer positioning apparatus and an eyepiece, for an ultrasonic arc scanning apparatus.

BACKGROUND

Ultrasonic imaging has found use in accurate measurement of structures of the eye, such as, for example, the cornea. Such measurements provide an ophthalmic surgeon valuable information that he can use to guide various surgical procedures performed on the cornea, one of the principal ones being the LASIK procedure for correcting refractive errors. They also provide diagnostic information after surgery has been performed to assess the geometrical location of corneal features such as the LASIK scar. This allows the surgeon to assess post surgical changes in the cornea as the cornea heals and to take steps to correct problems that can develop.

Ultrasonic imaging of the cornea presents a problem not generally encountered in other types of tissue. The corneal surfaces are necessarily smooth and spherically shaped to perform the optical function of focusing light rays. Because the corneal structures are smooth and regular, ultrasonic energy is reflected only in specific directions. In particular, an ultrasound beam from a transducer will only be reflected directly back to that transducer when the beam is aligned perpendicular to the corneal surface. This kind of reflective property is called specular reflection.

Because of the specular property of corneal surfaces, it will be appreciated that special care must be taken to align the transducer with the cornea at each position from which a partial image is to be formed. Ultrasonic imaging of large portions of the cornea can be accomplished by scanning the transducer along the cornea surface while continually adjusting the alignment of the transducer to provide a beam that is always directed toward the cornea's center of curvature.

Corneal imaging and measuring of corneal dimensions require that the scanning motion of the transducer be smooth and precisely aligned. Departures, even as small as 5 microns, of the transducer position from a circular path or of the beam's direction from the center of curvature can significantly degrade the resulting image. Mechanisms for performing the requisite scan alignment are described in U.S. Pat. Nos. 6,491,637 and 5,331,962 which are incorporated herein by reference. The reference "Ultrasonography of the Eye and Orbit", Second Edition, Coleman et al, published by Lippincott Williams & Wilkins, 2006 contains an excellent historical and technical summary of ultrasonic imaging of the eye and is incorporated herein by this reference.

While ultrasonic imaging may be used by ophthalmologists for quantitative analysis of laser refractive surgery, it may also be used for implantation of corneal and phakic lenses, implantation of intraocular lenses and specialty procedures such as glaucoma and cataract treatment.

Except for on-axis measurements, dimensions of eye components behind the iris cannot be determined by optical means. New procedures such as implantation of accommodative lenses may provide nearly perfect vision without spectacles or contact lenses. Implantation of accommodative lenses requires precision measurements of, for example, the lens width for successful lens implantation. Ultrasonic imaging can be used to provide the required accurate images of the lens especially where it attaches to the ciliary muscle which is well off-axis and behind the iris and therefore not accessible to optical imaging.

It must be appreciated that ultrasonic imaging requires a liquid medium to be interposed between the object being imaged and the transducer, which requires in turn that the eye, the transducer, and the path between them be at all times be immersed in a liquid medium. Concern for safety of the cornea introduces the practical requirement that the liquid medium be either pure water or normal saline water solution. In either case, the entire mechanism or major portions of it must be submerged in water for long periods.

Conventional mechanical components for guiding and controlling the motion of the transducer, such as journal, ball or roller bearings, are ill-suited for underwater operation. Films inevitably form on the bearing components, interfering with their smooth operation. Anti-fouling solutions cannot be added to the water because they introduce an unacceptable risk of injury to the patient's eye even if the eye is separated from the main body of the liquid by a thin, ultrasonically transparent barrier. Leaks through the barrier film or accidental perforation of the barrier film are an ever present possibility in a practical clinical device.

There remains, therefore, a need for a versatile scan head and transducer positioning apparatus; a water-proof arc scanning motor; an accurate transducer locator method; a fluid bearing method that can provide smooth scanning motion; and a disposable eyepiece, all of which are necessary for an improved ultrasonic arc scanning apparatus that can provide precision imaging for ophthalmology and optometry applications.

SUMMARY

These and other needs are addressed by the present invention. The various embodiments and configurations of the present invention are directed generally to ultrasonic imaging of biological materials such as the cornea and lens of the eye and in particular directed to components for an ultrasonic arc scanning apparatus such as a scan head positioning apparatus, a water-proof arc scanning motor, a fluidic bearing and an eyepiece, all of which can be used to, improve the accuracy, precision and ease of use of an ultrasonic arc scanning apparatus.

In one embodiment, a compact scan head positioning apparatus is disclosed. The function of this apparatus is to position the arc scanning assembly and ultrasonic transducer so that the transducer head is continuously following an arc guide centrated at a desired location. The arc guide has a radius of curvature that is approximately that of the eye component to be scanned. A successful scan often requires that the center of curvature of the arc assembly approximately match the center of curvature of the eye component of interest and that the scan head positioning apparatus be well-positioned to take advantage of the precision of a high-frequency ultrasonic pulse. A portion of the scan head positioning apparatus is installed in ambient air while a second portion of the scan head positioning apparatus containing the arc scanning head is installed in a chamber that is filled with water when operational. Thus, the scan head positioning apparatus should have both translating and rotating seals that function over distances and angles required to achieve the desired positioning of the arc scanning head relative to the component of the patient's eye to be scanned.

In another embodiment, a fluidic bearing mechanism is disclosed. The function of the bearing is to allow smooth motion of the transducer carriage assembly along the arc guide which has been positioned by a scan head positioning apparatus such as described above. A successful scan normally requires that the transducer assembly move smoothly along the arc guide to take advantage of the precision of a high frequency ultrasonic pulse.

In one configuration, the fluidic bearing mechanism is defined by a number of liquid flow passages in one or more of the arcuate guide. The liquid is pressurized to flow through the liquid passages and forms a liquid film along a selected interface between the guide assembly and carriage. A distance between the guide guide and carriage at the selected interface is greater than in the absence of the pressurized liquid.

In yet another embodiment, a motor capable of being operated safely under water is disclosed. The function of the motor is to move a transducer carriage assembly rapidly back and forth along a normally fixed arc guide so as to allow an ultrasonic scan of an eye component to be made.

In one configuration, the motor includes one or more magnets in one of the carriage and guide, and an iron-containing core surrounded by one or more electric coils in the other of the carriage and guide. In a preferred implementation, first and second magnets are in the carriage, and the electric coil and iron-containing core are in a guide track. The first and second magnets are positioned side-by-side, with the north-south polarities being opposed to one another. A long dimension of the electric coil(s) is adjacent to a face of the magnets to substantially maximize a propelling force. In a particularly preferred implementation, a mass of the carriage ranges from about 0.1 kg to about 0.3 kg. The electric coil is formed by a number of coil segments, with each of a number of subsets of the coil segments being powered selectively and independently by an electric circuit. A force caused by an electric current in a subset of the coil segments and local B-fields of the first and second magnets are in a common direction.

In another embodiment, a carriage location sensing device is provided to determine a location of the carriage relative to the guide assembly. The sensing device can have numerous configurations. In one configuration, the location sensing device includes a position encoder mounted on the carriage. The encoder senses a position of the carriage by reading a magnetic strip positioned along a length of the guide track. In another configuration, the location sensing device includes an optical encoder mounted on the carriage. The optical encoder senses a position of the carriage by illuminating a length of the guide track with light and sensing one or more of a refractive, diffractive, diffusive, and reflective distribution of light. For example, the encoder can illuminate a bar code positioned along a length of the arc guide. The bar code will produce a unique distribution of reflected light at any position along the length of guide. In another configuration, the locating sensing device includes a magnetic field sensor. The sensed magnetic field is related to a position along the guide. In yet another configuration, the location sensing device includes a mechanical counter. The mechanical counter produces a count, which is related to dimensional units and to a position along the guide.

Knowing the position of the carriage as a function of time can provide benefits. In a carriage motor having one or more magnets and an iron-containing core surrounded by electric coil segments, a controller, for example, can, at a selected point in time, selectively energize an electric coil segment in proximity to a sensed position of the carriage. The controller can, additionally or alternatively and at a selected point in time, selectively energize the transducer in response to a sensed position of the carriage to produce a non-uniform, desired physical spacing of ultrasound pulses. Position tracking is particularly beneficial where the carriage has a non-uniform velocity and/or acceleration along the guide. Simply put, the sensing device can provide precise position of the transducer carriage along the arc guide assembly which, in turn, allows for a precise and accurate ultrasonic scan to be made.

In yet another embodiment, three configurations of an eyepiece are disclosed. These all provide an acoustic path for ultrasonic scanning and separate the water in which the patient's eye is immersed, from the water in the chamber in which the positioning and arc guide assembly are contained. These configurations are relatively free from annoying leakage problems, are comfortable to the patient and can be manufactured for a low cost as the eyepiece should be replaced for every new patient. The different configurations incorporate different attachment and sealing mechanisms.

By way of example, a first configuration of an imaging device includes:
(a) an eyepiece for receiving an eye of a patient;
(b) a first liquid chamber in contact with an ultrasonic transducer;
(c) a second liquid chamber in contact with the patient's eye to be imaged by the ultrasonic transducer; and
(d) a barrier separating the first and second liquid chambers, wherein at least one of the following is true:
  (D1) the second liquid chamber comprises a drain port to drain liquid from the first liquid chamber; and
  (D2) the barrier is permeable to the liquid but impermeable to selected biological microbes, the microbes being selected from the group consisting of bacterium, virus, and fungus.

In another embodiment, a second configuration of an imaging device includes an eyepiece that includes a separate face seal ring. The face seal ring is filled with a liquid to better conform to a patient's face.

The following definitions are used herein:

An A-scan is representation of the reflected amplitudes of ultrasonic pulses emitted by an ultrasonic transducer as a function of time.

An accommodative lens, also known as a presbyopic lens or presby lens, is an intraocular lens implant that changes its focal distance in response to contraction of the ciliary muscle. When successfully implanted, an accommodative lens reverses presbyopia, the inability of the eye to change its focal distance from far to near.

Aligning means positioning the transducer and transducer carriage guide preferably accurately and reproducibly in space with respect to a feature of the eye component of interest (such as the center of curvature or boundary of the cornea, lens, retina, etcetera).

The anterior chamber comprises the region of the eye from the front of the eye to the iris.

The anterior segment comprises the region of the eye from the front of the eye to just beyond the back of the lens.

An arc scanner is a scanning device where the sensor moves in a substantially precise arc about the center of the area to be scanned with its beam constantly directed through a central point.

Arc scanning transducer center of curvature is the same as the center of curvature of the arc scanning guide.

Auto-centering means automatically, typically under computer control, causing centration of the arc scanning transducer with the eye component of interest.

A B-scan is representation of data as a by converting A-scan data using acoustic velocities to an image of the eye using grayscales which correspond to A-scan amplitudes.

A canthus is the angular junction of the eyelids at either corner of the eye where the upper and lower eyelids meet.

Centration means substantially aligning the center of curvature of the arc scanning transducer in space with the center of curvature of the eye component of interest (such as the cornea, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

A guide is an apparatus for directing the motion of another apparatus.

Haptics are little curved hair-like protrusions extending from the outer diameter of some types of artificial lenses. These haptics attach these lens to the ciliary muscle by protruding into the ciliary sulcus and allow the lens to accommodate in response to the action of the ciliary muscle.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after exposing it by cutting a thin flap, so as to reshape the external shape of the cornea.

A meridian is a plane that cuts through a portion of a three-dimensional component such as the cornea or natural lens of the eye and its angle is expressed relative to a horizon defined by the canthi.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ocular means having to do with the eye or eyeball.

Ophthalmology means the branch of medicine that deals with the eye.

Optical as used herein refers to processes that use light rays.

The optical axis of the eye is the line of best fit joining the centers of curvature of the refracting surfaces (the anterior and posterior surfaces of the cornea and lens).

Pachymetery or corneal pachymetery is technically referred to as Time Domain Reflectometry ultrasound. A pulse of ultrasonic energy is sent toward the cornea and the time spacing of the returning echoes are used to arrive at corneal thickness.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

The posterior chamber comprises the region of the eye from the back of the iris to the front of the lens.

The posterior segment comprises the region of the eye from the back of the lens to the rear of the eye comprising the retina and optical nerve.

Presbyiopia is typically caused by a loss of elasticity of the natural lens inside the eye. This occurs as part of the ageing process and, although it cannot be 'cured', it can be corrected by wearing glasses or implanting an artificial lens.

Refractive means anything pertaining to the focusing of light rays by the various components of the eye.

Registration means aligning.

Sector scanner is an ultrasonic scanner that sweeps out a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will only be reflected directly back to that transducer when the beam is aligned perpendicular to a specular surface.

The ciliary sulcus is the groove between the iris and ciliary body. The scleral sulcus is a slight groove at the junction of the sclera and cornea.

A track is an apparatus along which another apparatus moves.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

The visual axis of the eye is the line joining the object of interest and the fovea and which passes through the nodal points.

Zonules are tension-able ligaments extending from near the outer diameter of the crystalline lens. The zonules attach the lens to the ciliary body which allows the lens to accommodate in response to the action of the ciliary muscle.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

BRIEF DESCRIPTION OF THE DRAWINGS

FIG. 2 illustrates two different types of scanning strategies for ultrasonic scanners.

FIG. 13 illustrates the sealing method for the eyepiece of FIG. 12.

DETAILED DESCRIPTION

The embodiments described herein provide a superior design to prior art arc scanners. The embodiments disclose a scanning mechanism that is normally more tolerant of the underwater environment than prior art arc scanners. According to certain of the embodiments, an ultrasonic transducer is mounted to a transducer carriage that moves along a circularly curved guide. The carriage is typically guided by a guide, which is preferably configured as a track, so that the transducer beam axis is continuously directed towards a fixed center point regardless of the carriage's position along the guide. The guide assembly and the carriage have one or more smooth and precisely conforming surfaces that face one another and support a liquid film between them as described below.

The embodiments described herein are illustrated by an arc scanner in which the guide assembly is formed in the fixed shape of an arc that approximates the curvature of the eye's cornea or anterior lens surface. The guide may also have a variable shape such, as for example, two or more arcs or any continuously curved shape including a linear guide. The guide may also be flexible such that it can be controlled to conform to a desired shape. This latter embodiment would be useful for positioning a transducer carriage such that the transducer is aimed in a desired direction so as to better image any specular or non-specular component in an eye. Such flexing and aiming can be made in response to the changing shape of an eye component being imaged.

Ultrasonic Scanning Principles

Figure 1:
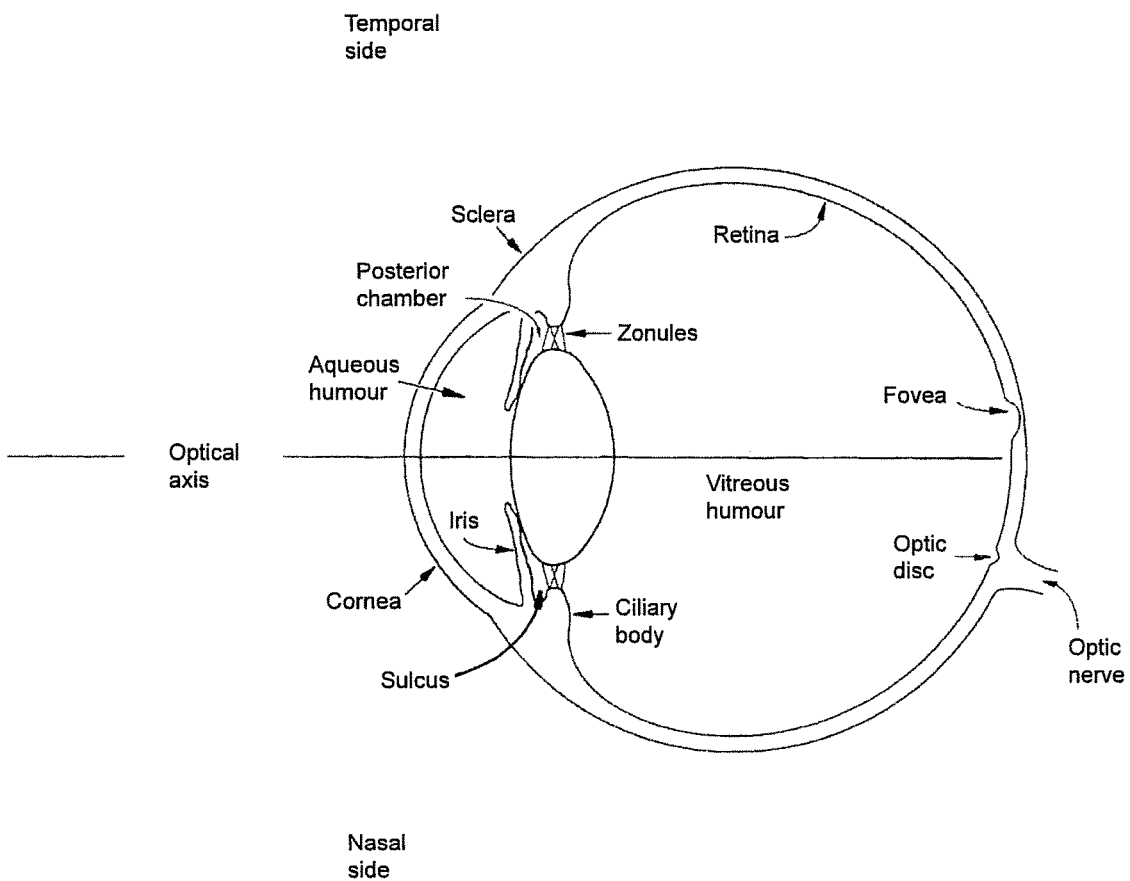
FIG. 1 is a schematic of the main elements of a human eye.

FIG. 1 is a schematic of the main elements of a human eye. The principal refracting components are the cornea, iris and lens. The cornea, which is optically transparent, is located at the front of the eye enclosing front of the anterior chamber. The iris separates the anterior chamber from the posterior chamber. The front of the lens encloses the back side of the posterior chamber. The natural lens sits directly behind the iris. Only the central part of the lens, which is behind the pupil, can be seen optically The anterior and posterior chambers comprise the anterior segment of the eye. The main volume or posterior segment of the eye lies behind the lens, with the retina and optical nerve at the rear of the posterior segment of the eye. The composition of the eye's aqueous and vitreous humour are very close to that of water with a density of about 1,000 kg/m$^3$, and this allows the eye to be a very good medium for the transmission of acoustic energy.

Optical means are suitable for viewing the anterior chamber and for viewing along the entire central axis of the eye. However, optical means cannot be used to view the portions of the posterior chamber lying immediately behind the iris, which includes the suspensory ligaments (called zonules), ciliary sulci and ciliary body. However, the eye components that cannot be viewed optically, can be viewed with high-frequency acoustic energy. As is well-known, acoustic frequencies in the ultrasonic range of about 10 MHz to about 60 MHz can be used to provide very high resolution images of, for example, the cornea and the lens.

FIG. 2 illustrates two different types of scanning strategies for ultrasonic scanners capable of imaging most regions of the interior of an eye. FIG. 2a illustrates the arc scanning principle for producing an ultrasonic scan of a component of an eye 201. In this type of scanner, which is described, for example, in U.S. Pat. Nos. 6,315,727, 6,491,637, 6,887,203 and 7,048,690, a transducer is moved in an arc whose center is set at a location of interest in the eye. In FIG. 2a, an ultrasonic transducer 203 is shown in a sequence of positions with the center of curvature of the arc guide 206 at approximately the center of curvature 202 of the cornea. The transducer 203 is moved in an arc as shown to produce many acoustic echoes (represented as rays 205) as it moves along the arc guide which can then be combined to form a cross-sectional image of the eye features of interest.

FIG. 2b illustrates the sector scanning principle for producing an ultrasonic image of a particular location with an eye 211. In this type of hand-held scanner, which is described, for example, in U.S. Pat. No. 6,198,956, an ultrasonic transducer 213 is shown being oscillated about a fixed position 212 so as to produce many acoustic echoes (represented as rays 215). These echoes can then be combined to form of a localized region of interest within the eye. The scanning principle illustrated in this figure is called sector scanning.

In both the arc and sector ultrasonic scanners, the transducer acts as both the transmitter and receiver of acoustic signals. The transducer emits a short acoustic pulse and then receives the reflected acoustic signal. This technique is described, for example, in U.S. Pat. No. 5,293,871 and in "Ultrasonography of the Eye and Orbit", Second Edition, Coleman et al, published by Lippincott Williams & Wilkins, 2006.

A sector scanner can be used to measure the thickness of an eye component such as, for example, the thickness of the cornea or the thickness of the lens along the optical axis. A sector scanner cannot be used to measure the length of specular features that extend laterally, such as, for example, the length of a LASIK scar, because only that small portion of the cornea that is perpendicular to the acoustic beam and reflects acoustic energy back to the transducer is visible to a sector scanner. With a sector scanner, the patient is typically required to be supine.

An arc scanner, on the other hand, can be used to measure the thickness of an eye component such as, for example, the thickness of the cornea or the thickness of a lens as well as to measure the length of specular features that extend laterally, such as, for example, the length of a LASIK scar or the lateral length of a natural or implanted lens. In an arc scanner, the patient is typically looking downward at approximately 45 degrees from horizontal. This is a preferred position and has relevance to the design of an eyepiece described in FIGS. 10 through 12.

Both arc and sector scanners are discussed on page 35 of "Ultrasonography of the Eye and Orbit", Second Edition, Coleman et al, published by Lippincott Williams & Wilkins, 2006.

Figure 3:
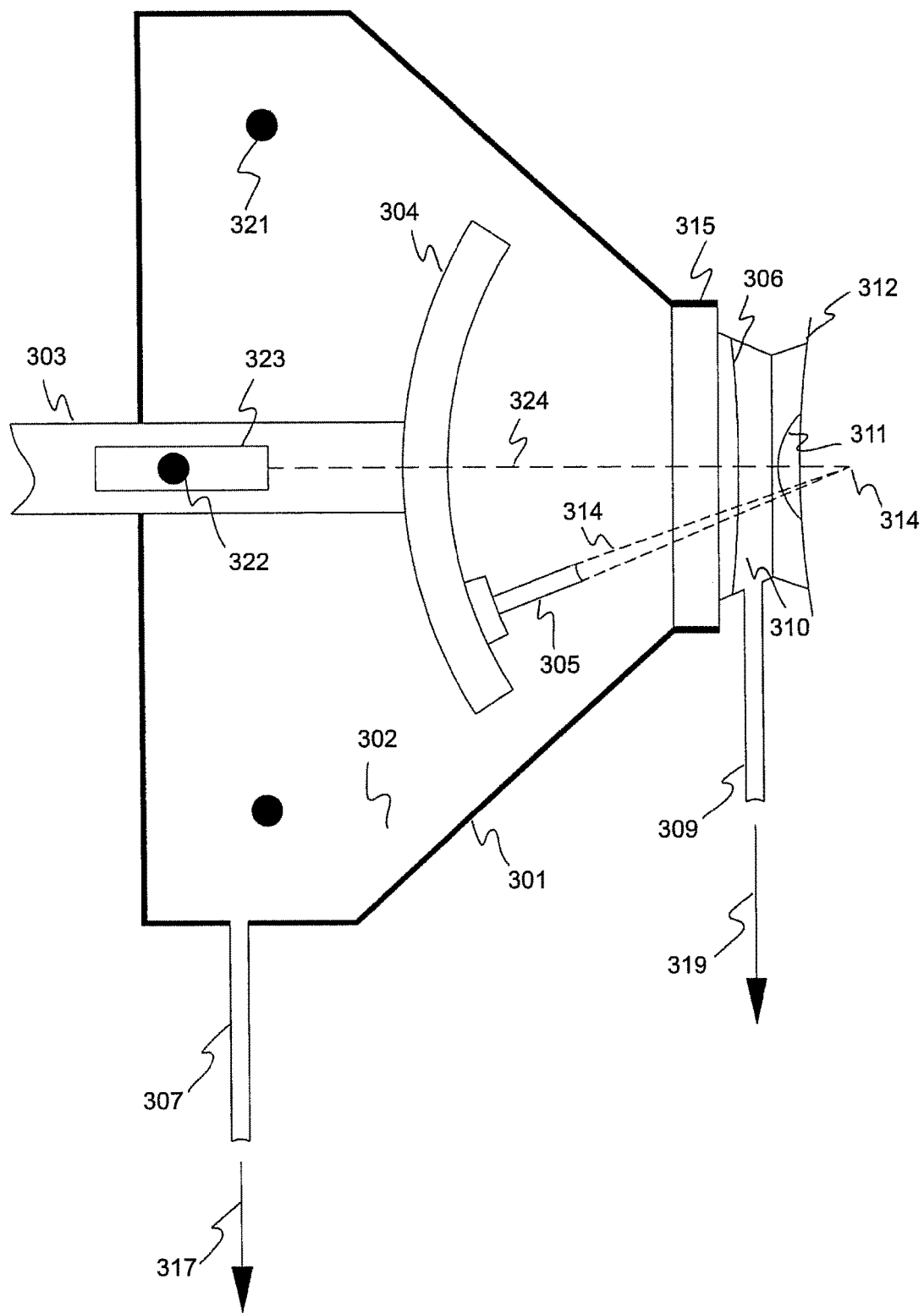
FIG. 3 is a schematic of an arc scanning device.

FIG. 3 shows the main elements of an arc scanning device illustrating positioning of a transducer along an arc guide whose center of curvature is centered approximately on the center of curvature of an eye component of interest. FIG. 3 shows fixation lights 321 and 322 that allow the patient to fixate his or her eye to maintain it in a steady position during scanning. FIG. 3 also shows an optical video camera 323 which may be used by the operator of the arc scanner to monitor the position of the patient's eye and to determine whether the patient's eye is open before a scan is initiated. The transducer and its arc guide assembly are immersed in a chamber of water 302 to provide a transmission path for the acoustic signals. The patient's eye must also be immersed in water to provide continuity of the transmission path for the acoustic signal. FIG. 3 also shows a hygienic barrier 306 which separates the water chamber 301 in which the transducer 305 and arc guide assembly 304 are contained from the water 310 in which the patients eye is immersed. This barrier 306 provides the separation of water 302 in which the transducer 305 and arc track assembly 304 are contained from the water 310 in which the patients eye is immersed. The arc guide assembly and associated components may be contaminated, for example, by particles from wearing mechanical components. The water 310 in which the patients eye is immersed may be contaminated by bacteria or virus particles from the patient. As can be appreciated, the water 310 in which the patients eye is immersed should be changed for every patient to prevent possible disease transmission. As can be further appreciated, the hygienic membrane 306 must be substantially transparent to ultrasound so as to maintain a clear acoustic transmission path between the patient's eye and the ultrasonic transducer. The hygienic membrane 306 is typically formed as part of a disposable eyepiece such as described in FIGS. 10 through 12.

References are made herein to a medium suitable for conducting acoustic energy in the form of ultrasound. There are reasons to prefer that the medium be pure water or physiologic saline (also known as normal saline) but the embodiments do not exclude other media suitable for conducting acoustic energy in the form of ultrasound. Most other media present an increased danger to the patient's eye, even with a barrier interposed between the eye and the ultrasonic transducer. Barriers can leak or be breached, allowing the liquids on either side to mix, thus bringing a potentially harmful material into contact with the eye.

It should be appreciated, however, that non-harmful, less-corrosive media and leakproof, impenetrable barriers might be developed or discovered. This might allow different media than pure water or physiologic saline to be used in this invention. Nothing about embodiments herein other than the hazards just described requires pure water or physiologic saline to be present in the chamber containing the transducer. All references to water in the following should accordingly be understood as referring to any suitable liquid.

FIG. 3 illustrates the continuity of an acoustic transmission path through water. A chamber 301 of water 302 is shown with a positioning arm 303 and arc guide assembly 304 on which an ultrasonic transducer 305 is mounted. An ultrasonically transparent barrier 306 separates chamber 301 from the interior of an eyepiece 308. The eyepiece 308 contains a separate volume of water 310 which fills the interior of the eyepiece 308 and contacts a patient's eye surface 311. The eyepiece 308 is connected and sealed to the main chamber 301 of the arc scanning device, and is also sealed against the patient's face 312. As can be seen, there is a continuous path through water from the transducer 305 to the patient's eye surface 311 for the efficient passage of acoustic energy. The barrier 306 readily passes acoustic energy without alteration, thus forming a portion of the continuous path between the transducer 305 and the patient's eye surface 311. Since the acoustic impedance of the patient's eye is approximately that of water, the acoustic energy from the transducer can be efficiently transmitted into the eye and reflected back from an eye component, such as for example, the surface of the cornea, to the transducer. Also shown in FIG. 3 are a water fill tube 307 for the main chamber 301 and a separate water fill tube 309 for the eyepiece 308. As can be appreciated, the water used in the eyepiece can be distilled or slightly saline to match the salinity of the eye, and the water used in the eyepiece can be introduced at a temperature that is comfortable for the patient.

Components of the Present Invention

Scan Head Positioning Apparatus

The function of a scan head positioning apparatus is to position the arc scanning head assembly and ultrasonic transducer so that the transducer head is continuously on an arc guide that is positioned such that its center of curvature is at the approximate center of curvature of the eye component to be scanned. A successful scan often requires that the radius of curvature of the arc assembly approximately match the radius of curvature of the eye component of interest and that the scan head positioning apparatus be accurately positioned to take advantage of the precision of a high frequency ultrasonic pulse.

Figure 4:
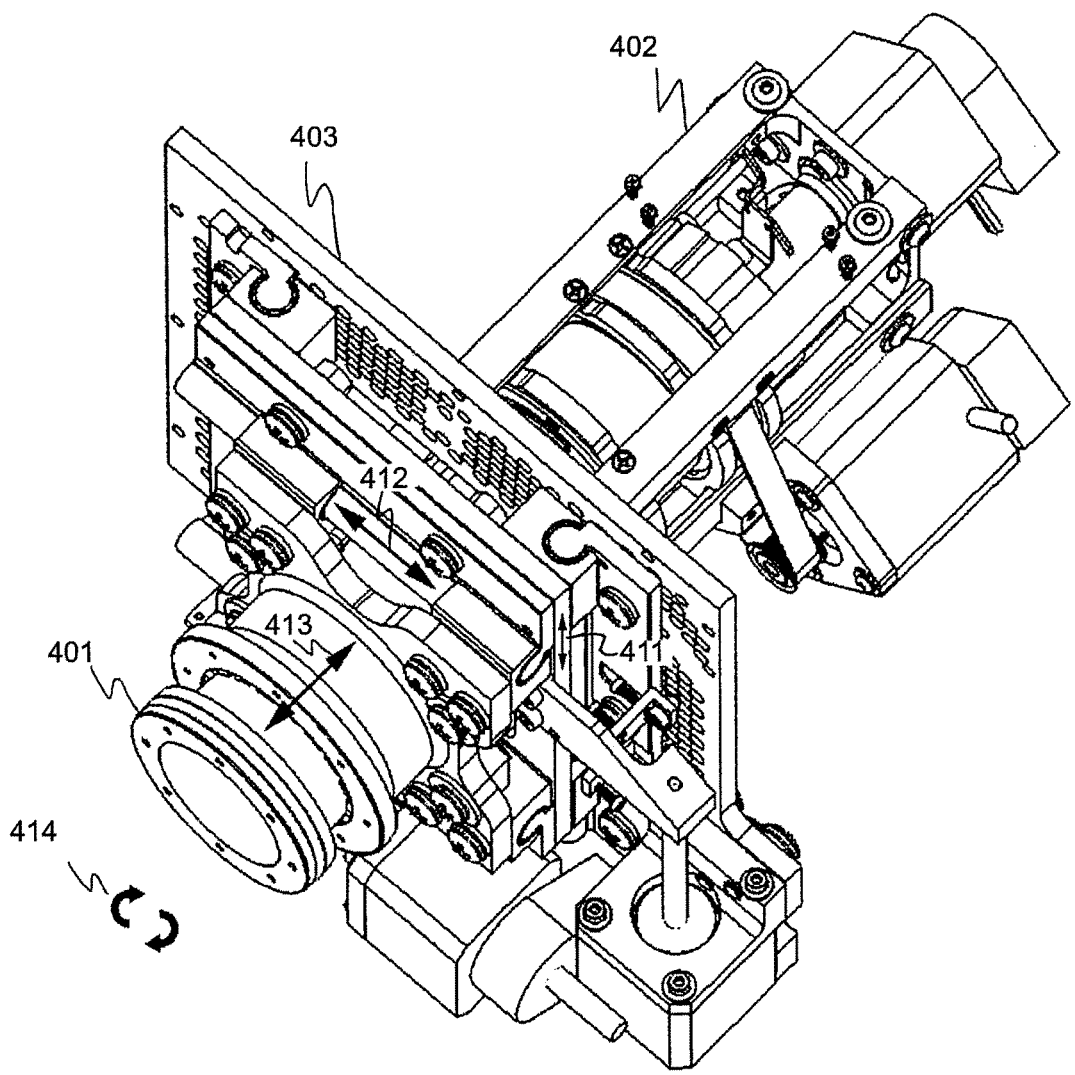
FIG. 4 illustrates an isometric view of a compact arc scanning head positioning mechanism.

FIG. 4 illustrates an isometric view of a compact scan head positioning mechanism. An axial carrier frame 402 and mounting plate 403 are fixed to the main arc scanner assembly. The scanner head mount arm 401 can move axially back and forth as shown by arrow 413. The scanner head mount arm 401 can rotate about its axis as shown by arrows 414. The scanner head mount arm 401 can move up and down as shown by arrows 411 and back and forth as shown by arrows 412. The scan head, which is mounted on the scanner head mount arm 401, is not shown in this figure.

Figure 5:
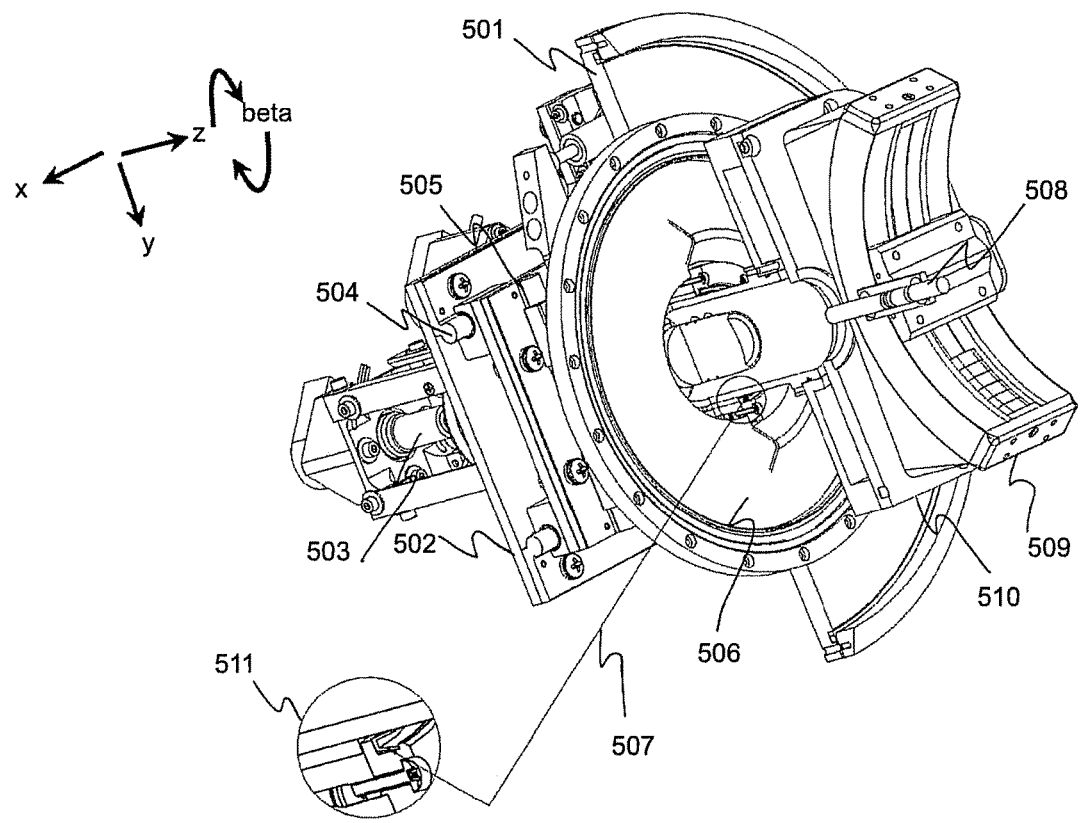
FIG. 5 further illustrates a compact arc scanning head positioning mechanism.

FIG. 5 further illustrates a compact scan head positioning mechanism. FIG. 5 shows an arc scanner head 509 with ultrasonic transducer 508 mounted on the end of a scanner head mount arm 510. These components (scanner head mount arm 510, scanner head 509 and ultrasonic transducer 508) are operative under water and are sealed from the rear portion of the positioning mechanism by a translational seal 506 and a rotational seal 507. The translational seal 506 is preferably formed by a large rubber membrane that can flex with the small x and y motions required by the scanning head positioner, though any sealing mechanism may be employed. The z-axis seal and rotational seal 507 are attached to a stationary plate 501 which is affixed to the main arc scanner assembly. The z-axis and rotational seal 507 is typically formed by a circumferential groove type sealing mechanism with the groove facing into the water, though any sealing mechanism may be employed. The seal is preferably a commercially available seal from SealScience, model 810V. It allows both rotation and axial translation of the center tube while maintaining a water tight seal. The cross section of the seal is such that increased water pressure acts on the seal in a way that increases radial sealing force. The sealing surfaces are preferably anodized aluminum. Stationary plate 502 is also affixed to the main arc scanner assembly. The scanning head can be moved back and forth axially (the z-direction) by axial piston 503 or another suitable mechanism. The scanning head can be rotated (the beta-direction) about the z-axis by a rotary stepping motor (not shown) or another suitable device. The scanning head can be moved up and down (the y-direction) by piston 505 or another suitable mechanism. The scanning head can be moved from side to side (the x-direction) by piston 504 or another suitable mechanism. The components to the left or rear of stationary plate 501 remain in ambient air while the components to the right or font of stationary plate 501 are in immersed in water when the arc scanner is operational.

Magnetic Sensing System

The carriage can be moved along the arc guide using any of a number of motive methods. In the preferred embodiment, the guide track contains windings arranged so that they together with the magnets in the carriage form a linear motor (described below in FIGS. 8 and 9). Also in the preferred embodiment, there is a position encoder, preferably incremental and magnetic, borne by the guide track and the carriage, that allows external circuitry to sense the position of the carriage along the track. The positional information is used to control which windings are energized as the carriage moves along the track. It is also used to trigger the sending of ultrasonic pulses so as to provide, for example, a uniform physical spacing of the pulse-echo tracks in an ultrasound B-scan image. As can be appreciated, the positional information can be used to trigger the sending of ultrasonic pulses so as to provide a non-uniform but desired physical spacing of the pulse-echo tracks in an ultrasound B-scan image.

Figure 6:
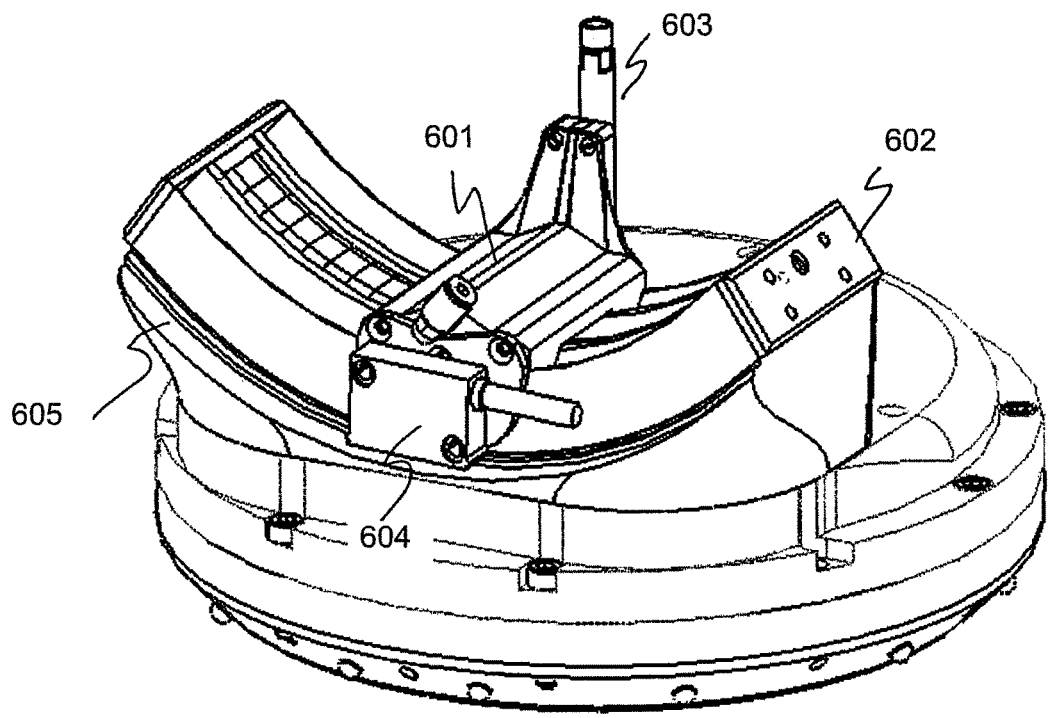
FIG. 6 illustrates a magnetic positioning system.

FIG. 6 illustrates a magnetic positioning system. This positioning system provides precise position information for the transducer carriage along the arc guide assembly which, in turn, allows for a precise and accurate ultrasonic scan to be made. FIG. 6 shows a scan head mounted on a scan head positioning assembly described previously. The scan head consists of an arc guide assembly 602 and a transducer carriage assembly 601. Transducer 603 has been described previously. An OTS magnetic encoder (such as for example a Siko MSK5000) is contained in a housing 604 mounted on the side of the transducer carriage assembly 602. The magnetic encoder senses its position by reading a magnetic strip 605 (shown as a black strip underneath the housing 604) which is attached to the arc guide track. The magnetic strip 605 is a flexible magnetic material with alternating north/south poles and with a distance between poles known to the encoder. The encoder then outputs standard quadrature encoder pulses as it moves along the magnetic strip. This model of encoder with the recommended magnetic strip delivers a 1 micron resolution or about 0.0005 degrees at the radius of the arc scanner.

The magnetic positioning system is based on a home position on the arc guide track for the arc carriage and a series of magnetic combs installed along the arc guide track and whose spacings are accurately known. A coil in the arc carriage then counts current pulses as the carriage passes over the magnetic combs to determine a precise position of the carriage along the arc guide track. Other position sensing systems are possible. These include optical systems (optical bars replace the magnetic combs), mechanical systems and electrical systems (such as a potentiometer). The magnetic sensing system is preferred over the optical system which requires periodic cleaning and the mechanical system which is subject to buildup of mineral and other deposits.

Fluidic Bearing

A bearing mechanism is another component of an arc scanner. The function of the bearing is to allow smooth motion of the transducer assembly along the arc guide assembly which has been positioned by a scan head positioning apparatus such as described above in FIGS. 4 and 5. A successful scan normally requires that the transducer assembly move smoothly and without jitter or jerk along the curved arc guide assembly to take advantage of the precision of a high frequency ultrasonic pulse (in physics, jerk is the rate of change of acceleration; more precisely, the derivative of acceleration with respect to time, the second derivative of velocity, or the third derivative of displacement).

The carriage has a set of liquid passages that communicate with a source of liquid under pressure. The liquid passages also communicate with ports located on the smoothly conforming aspect of the carriage that meets a matching surface on the arc guide track to form a fluidic bearing. The liquid flows from the source through the passages to and through the ports, forming a liquid film between the carriage and the arc guide track. The pressure from the ports and in the liquid film urges or forces the carriage and the arc guide track apart, causing them to separate, reaching an equilibrium position with a thin film of liquid flowing out from between them. Following known practice in fluidic bearings, the size of the passages is chosen to make the pressure at each port largely independent of the flow through the other ports to provide stability to the fluidic bearing. It is preferred that the passages and exit ports are in the transducer carriage rather than in the arc guide track so that the ports are always covered, an arrangement that reduces the liquid mass flow requirement.

As will be described below, a linear motor is used to propel the transducer carriage along the arc guide. The permanent magnets in the transducer carriage attract the carriage to the arc guide with considerable force. This makes it possible to use a fluidic bearing system as the fluid pressure generated force can be made to approximately balance the magnetic attraction force. This minimizes any mechanical drag of the transducer carriage on the arc guide and allows the system to move smoothly and without jitter.

Figure 7:
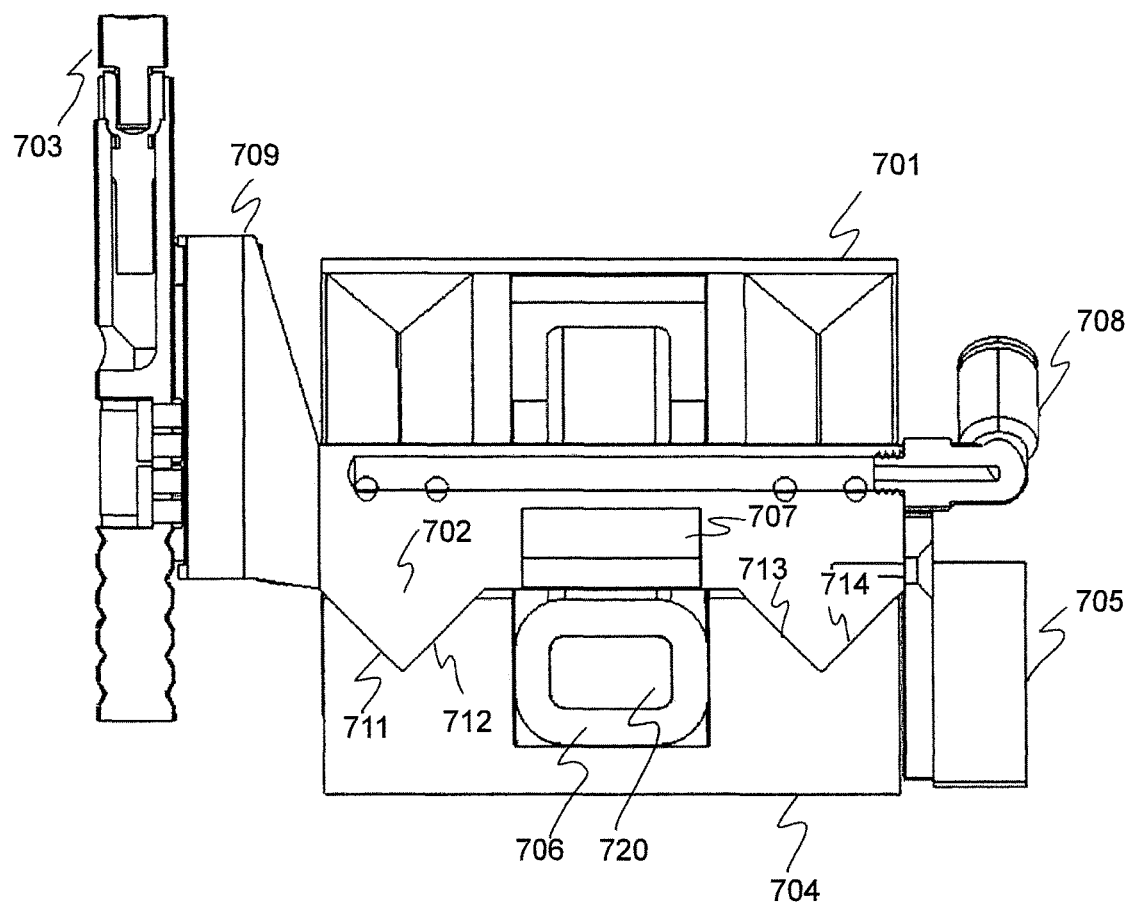
FIG. 7 illustrates a fluidic bearing operative between a fixed arc assembly and a moving transducer assembly.

FIG. 7 illustrates a fluidic bearing operative between a fixed arc guide assembly 704 and a moving transducer carriage assembly 702. It is understood that once the arc guide assembly 704 has been moved into position and secured by the positioning mechanism described in FIGS. 4 and 5, the motion of the transducer carriage assembly 702 is constrained to be along the arc guide assembly 704 for subsequent scanning operations. The view shown in FIG. 7 is a normal section through the arc guide assembly 704 and a moving transducer carriage assembly 702, with the rest 701 of the arc guide assembly 704 curving upward in the background. The arc guide assembly 704 contains linear motor coil elements 706 and their iron cores 720 which will be described further in FIGS. 8 and 9. The moving transducer carriage assembly 702 includes an ultrasonic transducer 703, a transducer mount 709 and a magnetic sensor housing 705. A water hose (not shown) is connected via fluid coupling 70. An electrical conduit that transmits electronic signals to and from the transducer and transmits electronic signals to and from a position sensing means is not shown but is also attached to the transducer carriage assembly 702. The position sensing means for determining the relative position between the moving transducer carriage assembly 702 and the arc guide assembly 704 may be, for example, a magnetically coded strip along the arc guide assembly 704 and a magnetic sensing element on the moving transducer carriage assembly 702, such as described in FIG. 6.

The ability to accurately detect the relative position between the moving transducer carriage assembly 702 and the arc guide assembly 704 can be important because it can accommodate non-uniform motion of the moving transducer carriage assembly 702. For example, the transducer carriage assembly 702 may accelerate from rest at one end of the arc guide, reach a maximum velocity which may be maintained briefly near the center of the arc guide and then decelerate to rest at the opposite end of the arc guide. As a result of knowing the transducer carriage assembly 702 position along the arc guide, the pulsing and receiving periods of the transducer 703 can be programmed to correlate with the motion the transducer 703 along the arc guide so that a coherent image may be formed. The ability to operate with a non-uniform transducer carriage assembly 702 motion is enabled by the smooth acceleration and deceleration allowed by the fluidic bearing. FIG. 7 shows the bearing surfaces 711, 712, 713 and 714 between the arc guide assembly 704 and the moving transducer carriage assembly 702.

Since the entire arc scan head assembly is under water, it is natural to use a fluid bearing where the fluid is also water. The fluid is pressurized by a small pump mounted on the transducer carriage assembly 702 and water is pumped through small holes located at regular intervals along the bearing surfaces 713 and 714 of the transducer carriage assembly 702. The water in the main arc scan head chamber is commonly at approximately 1 bar or ambient pressure.

The pump delivers fluid at pressures typically in the range of ½ to 2 bars above ambient pressure. The pressurized fluid then lifts the transducer carriage assembly 702 about 5 to about 10 microns off the surface of the arc guide assembly 704 and maintains this separation while fluid is continuously pumped through the small holes located along the bearing surfaces 713 and 714 of the transducer carriage assembly 702.

As has been shown experimentally, the linear motor cannot move the transducer carriage assembly 702 until the fluid bearing is activated because of the strong attractive force between magnets 707 and iron cores 720. Once the fluid is being pumped through the small holes located along the bearing surfaces 713 and 714 of the transducer carriage assembly 702, the transducer carriage assembly 702 rises to achieve a separation of a few microns and moves freely and without jerk along the arc guide track.

Linear Motor

The function of the motor is to move a transducer carriage assembly along an arc guide assembly so as to allow an ultrasonic scan of an eye component to be made. The linear motor must be able to be operated safely under water since the entire arc scanning head is immersed in water.

The following descriptions assume that the linear motor has magnets in the carriage and windings in the circular track. It should be noted that this could have been reversed, with the magnets in the circular track and the windings in the carriage, without changing the fundamental operation of the scanning system. Placing the magnets in the carriage represents the preferred embodiment and the best mode known to the inventors.

The transducer carriage has one or more magnets affixed to it, and the track is made of or contains magnetic material such as iron. The magnets are arranged in the carriage so that the resulting magnetic field urges or attracts the carriage toward the track. Because the entire track and the carriage must be submerged in water during normal operation, the magnetic components are protected from corrosion by either choosing the exposed iron material to be a magnetic stainless steel or by sealing the iron in a material such as epoxy to protect it from water exposure.

The transducer carriage assembly typically weighs in the range of about 0.1 kg to about 0.3 kg. This range of carriage assembly mass is light enough to allow rapid acceleration and deceleration yet heavy enough to provide sufficient inertia to filter out extraneous mechanical jitter in the motion of the transducer carriage along the arc guide track. The location of the center of mass of the transducer carriage is also important as it is desired that the carriage be reasonably balanced on the guide track.

Figure 8:
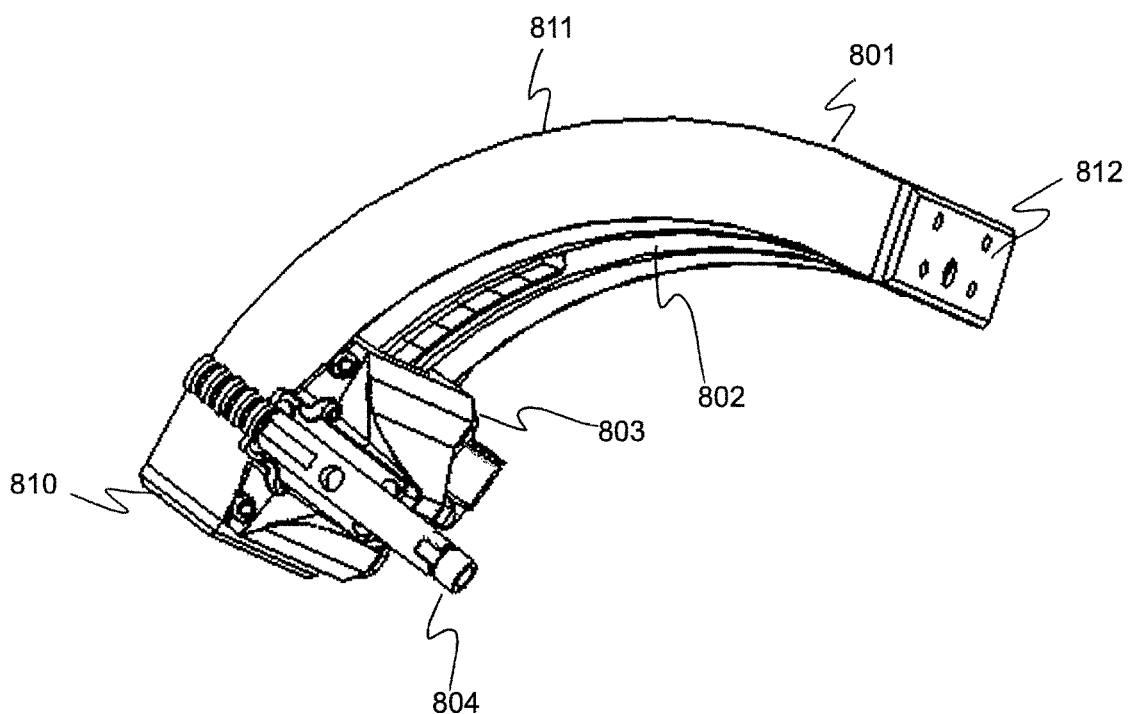
FIG. 8 is an isometric schematic of a linear induction motor to move a transducer assembly along a fixed arc assembly.

FIG. 8 is an isometric schematic of an apparatus containing a linear induction motor to move a transducer carriage assembly 803 along an arc guide assembly 801. FIG. 8 shows a transducer assembly 803 with an ultrasonic transducer 804. The ultrasonic transducer 804 is mounted such that it always points at the center of curvature of the arc defined by the radius of curvature of arc guide assembly 801. The transducer carriage assembly 803 moves along an arc guide assembly 801, propelled by a linear induction motor arrangement. The motion of the transducer carriage assembly 803 may be non-uniform. For example, the transducer assembly 803 may accelerate from rest at one end 810 of the arc guide assembly 801, reach a maximum velocity which may be maintained briefly near the center 811 of the arc guide assembly 801 and then decelerate to rest at the opposite end 812 of the arc guide assembly 801. In a preferred embodiment, permanent magnets are installed in the transducer carriage assembly 803 and electrically powered field coils are installed down a central groove formed in the in the fixed arc assembly 801. An example of such a groove and field coils can be seen in FIG. 7 with field coils 706 positioned in a groove in the arc guide assembly 704.

Figure 9:
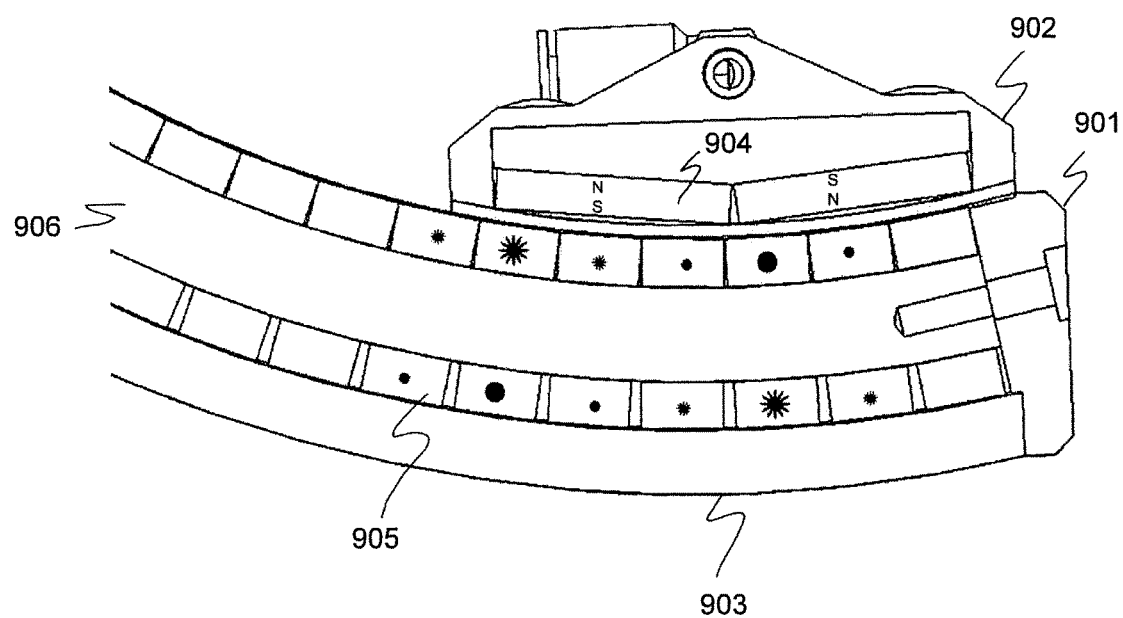
FIG. 9 shows a schematic of the currents and magnetic forces that propel a transducer carriage along an arc guide track.

FIG. 9 shows a schematic of the currents and magnetic forces that propel a transducer carriage along an arc guide assembly 903. A transducer carriage 902 is shown with two permanent magnets 904 mounted side-by-side but with their north-south polarities on opposite faces. The two permanent magnets 904 are preferably of equal size. A carriage track 903 which forms an arc is shown with several wound conductive coils 905, wound around an iron core 906 which is also formed as an arc in this side view. The coils 905 are approximately rectangular in cross section as shown, for example, in FIG. 7 by callout 706. The long side of the rectangular coil windings is preferably adjacent to the face of the magnets to maximize propelling force (this force is described below). The coils 905 may be made of any conductor material such, as for example, copper, aluminum and the like. The coils 905 are preferably sized and spaced such that three adjacent coils are approximately the same width as either one of the permanent magnets 904. Starting at either end of the arc guide, each set of three adjacent coils is powered by a 3 phase electrical circuit. The 3 phase circuit voltages are controlled by a Pulse Width Modulated (PWM) system that is in turn controlled by the position of the transducer carriage 902. The position of the transducer carriage 902 relative to the arc guide 903 is determined, for example, by a magnetic strip sensor system such as described in FIG. 6. The combination of PWM; an accurate location sensing system; a fluid bearing between the arc guide and the transducer carriage (described in FIG. 7); and the mass of the transducer carriage provides a very smooth motion of the transducer carriage 902 which is essential to making sharp, precision high-frequency acoustic measurements (approximately 3 MHz to approximately 60 MHz).

In this application, it is preferable to embed the permanent magnets 904 in the moving transducer carriage 902 and to embed the coils 905 in the arc guide assembly 903. Embedding the permanent magnets 904 in the moving transducer carriage 902 adds mass to the transducer carriage assembly 902 which helps to keep its motion along the arc guide track smooth. Embedding the coils 905 in the arc guide assembly 903 reduces the motion in the water of the electrical wires connecting the power source with the coils since the motion from positioning the scan head is far less than the motion of the transducer carriage back and forth along the arc guide track. This is a slightly less energy efficient design for a linear motor since all the coils are energized by the 3 phase power supply. However, motor efficiency is not a major concern in this application.

With the transducer carriage position shown in the example of FIG. 9, the gap between the permanent magnets 904 is lined up with the gap between two adjacent coils 905 such that three coils 905 are centered beneath each permanent magnet 904. The current is at a maximum in the two coils centered beneath each permanent magnet but in opposing directions as indicated by the current arrows represented by an end view of an arrow feather and an end view of an arrow head. The current is low but in the same direction in the coils adjacent to the coils carrying the maximum current, as indicated by the smaller current arrows. In this position, there is a force exerted on each of the magnets 904 along the same direction of the arc 903. Since the magnets 904 are embedded and attached to the transducer carriage 902, the transducer carriage 902 is propelled along the arc guide assembly.

In this example, the coils 905 are wound around an iron core which is approximately rectangular in shape (although with rounded corners so as not to cut the coil wire as shown for example in FIG. 7 by callout 706). The propelling force arises from the current in the coil elements adjacent to the permanent magnets interacting with the local magnetic field of the permanent magnets according to the well-known equation:

$$dF = I\, dl \times B$$

where
dF is the differential force
I is the total current (number of windings times current in each winding)
dl is a differential length of coil winding
X represents the cross-product between dl and B
and B is the local magnetic field of the permanent magnet As can be seen, the force is orthogonal to both the direction of the current and the direction of the local B-field and so the force on the permanent magnets is along the arc guide assembly. It is noted that the force is caused by the current in the coil winding elements adjacent to the permanent magnet. The force caused by the current in the coil winding elements distant from the permanent magnet is in the opposite direction but is very weak as it is effectively shielded by the iron core 906. The force caused by the current in the coil winding elements normal to the arc track are largely parallel to the magnetic field of the permanent magnets and so do not contribute to the propulsive force on the transducer carriage 902.

The permanent magnets 904 are held in place with a back iron component whose face is flush with the pole faces of the permanent magnets. The back iron with the two permanent magnets 904 thus form, in essence, a horseshoe magnet and can in fact be replaced by an appropriately shaped horseshoe magnet. A magnetic circuit is thus formed by the back iron, the permanent magnets 904 and the iron core 906.

Eyepiece

An eyepiece serves to complete a continuous acoustic path for ultrasonic scanning, that path extending from the transducer to the surface of the patient's eye. The eyepiece also separates the water in which the patient's eye is immersed from the water in the chamber in which the arc track assembly are contained. Finally, the eyepiece provides a steady rest for the patient and helps the patient to remain steady during a scan. To be practical, the eyepiece should be free from frequent leakage problems, should be comfortable to the patient and its manufacturing cost should be low since it should be replaced for every new patient.

Figure 10:
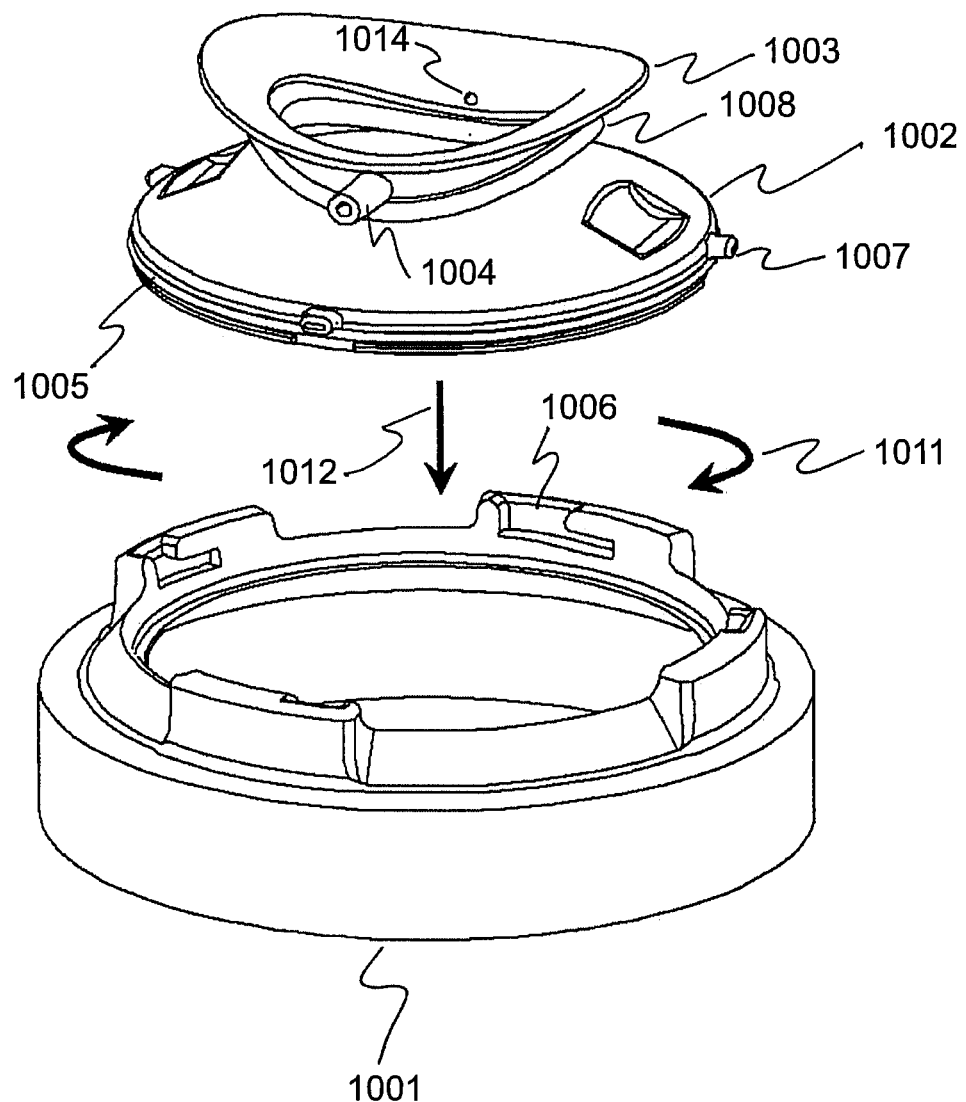
FIG. 10 illustrates an embodiment of an eyepiece for an arc scanner.

FIG. 10 illustrates an embodiment of an eyepiece that satisfies these requirements. The eyepiece consists of a mounting ring 1001 and an eye seal ring 1002. The mounting ring 1001 is attached to and is typically a permanent part of the main arc scanner assembly. As shown here the mounting ring 1001 has several attachment grooves 1006 which can accept attaching mechanisms 1007 on the eye seal ring 1002. In this embodiment, the attaching mechanisms 1007 are pushed down 1012 into the attachment grooves 1006 and then rotated 1011 into position to form a mechanical connection that seals the eye seal ring 1002 against the mounting ring 1001 to prevent water leakage. This is also known as a bayonet type connection. There may be a sealing ring

1005 which is compressed as the attaching mechanisms 1007 are rotated 1011 into position. The eye seal ring 1002 has a soft rubber or foam contoured face seal 1003 which is designed to seal against a typical human face around the eye that is to be scanned. The eye seal ring 1002 is also shown with its water fill tube 1004 on the top and a water drain tube 1014 on the bottom. A sealed hygienic barrier (not shown) is formed as part of the eye seal ring 1002 during manufacture and is typically located where the contoured face seal 1003 is connected at location 1008 to the main body of the eye seal ring 1002.

The hygienic barrier or membrane may be permeable or semi-permeable to water as long as it is impermeable to bacteria, viruses, fungi, and other potentially harmful biological and chemical impurities. The membrane is preferably impermeable to water to provide superior isolation from biological and non-biological impurities that may be dissolved or carried in water. The membrane is preferably optically clear to allow a video camera to view the eye (see FIG. 3) through the membrane. The membrane preferably passes acoustic pulses without significant energy absorption or reflection. These conditions can be substantially met by a membrane that is thinner than an acoustic pulse wavelength. Eyepiece membranes have been made from materials such as, for example, polyethylene, mylar, polypropylene; vinylidene chloride; polyvinylidene chloride; or DuraSeal (made by Diversified Biotech) which is polyethylene based and free of and adhesives. A preferred material is medical grade polyethylene which has an acoustic impedance only somewhat higher than that of water (about 2.33 million $kg/m^2$-s compared to 1.54 million $kg/m^2$-s for water). The thickness of the membrane is preferably in the range of about 10 to about 30 microns. This thickness is a small part of an acoustic wavelength in water which is about 150 microns at 10 MHz and about 20 microns at 80 MHz.

Figure 11:
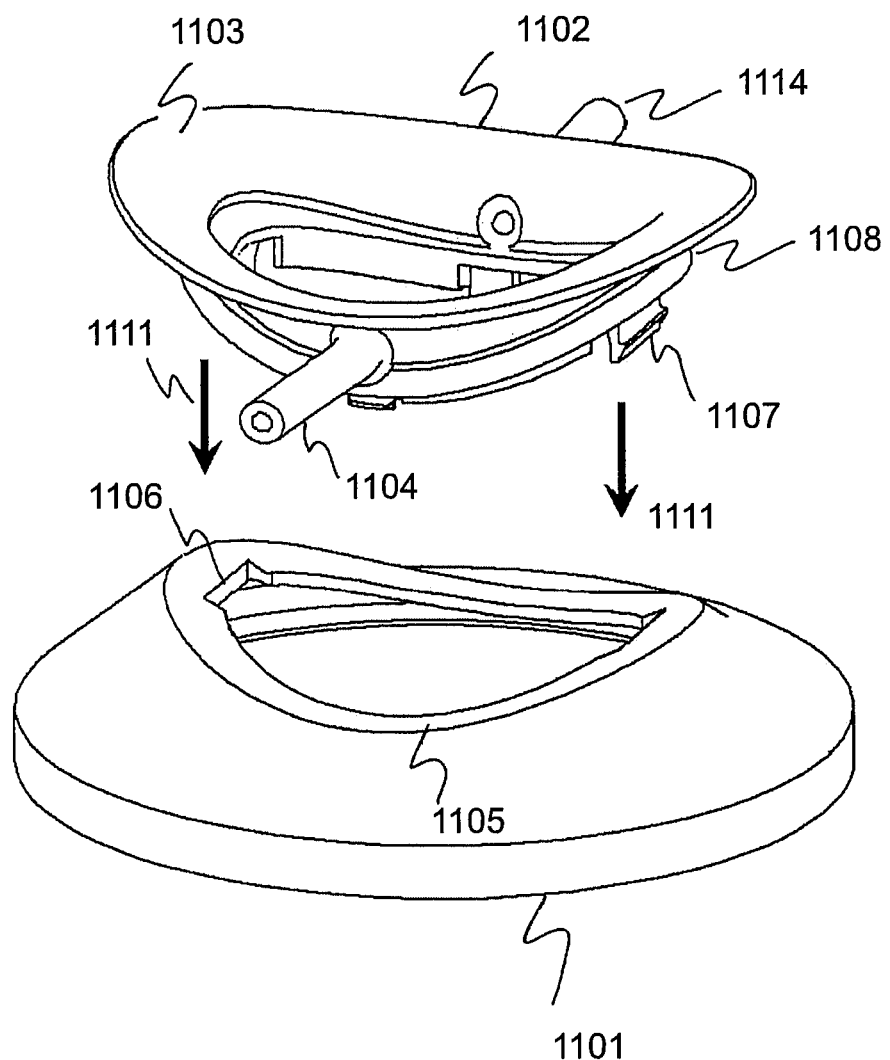
FIG. 11 illustrates an alternate embodiment of an eyepiece for an arc scanner.

FIG. 11 illustrates an alternate embodiment of an eyepiece that also satisfies the practical requirements described above. The eyepiece consists of a mounting ring 1101 and an eye seal ring 1102. The mounting ring 1101 is attached to and is typically a permanent part of the main arc scanner assembly. As shown here the mounting ring 1101 it has several attachment grooves 1106 which can accept attaching mechanisms 1104 of an eye seal ring 1102. In this embodiment, the attaching mechanisms 1104 are pushed down 1111 into the attachment grooves 1106 and then snapped into position to form a mechanical connection that seals the eye seal ring 1102 against the mounting ring 1101 to prevent water leakage. This is also known as a snap-on type connection. There may be a sealing surface 1105 on the mounting ring 1101 and a matching sealing surface (not shown) on the eye seal ring 1102 which is compressed when the attaching mechanisms 1104 are snapped into position. The eye seal ring 1102 has a soft rubber or foam contoured face seal 1103 which is designed to seal against a typical human face around the eye that is to be scanned. The eye seal ring 1102 is also shown with its water fill tube 1104 on the top and a water drain tube 1114 on the bottom. A sealed hygienic barrier (not shown) is formed as part of the eye seal ring 1102 during manufacture and is typically located where the contoured face seal 1103 is connected at location 1108 to the main body of the eye seal ring 802.

Figure 12:
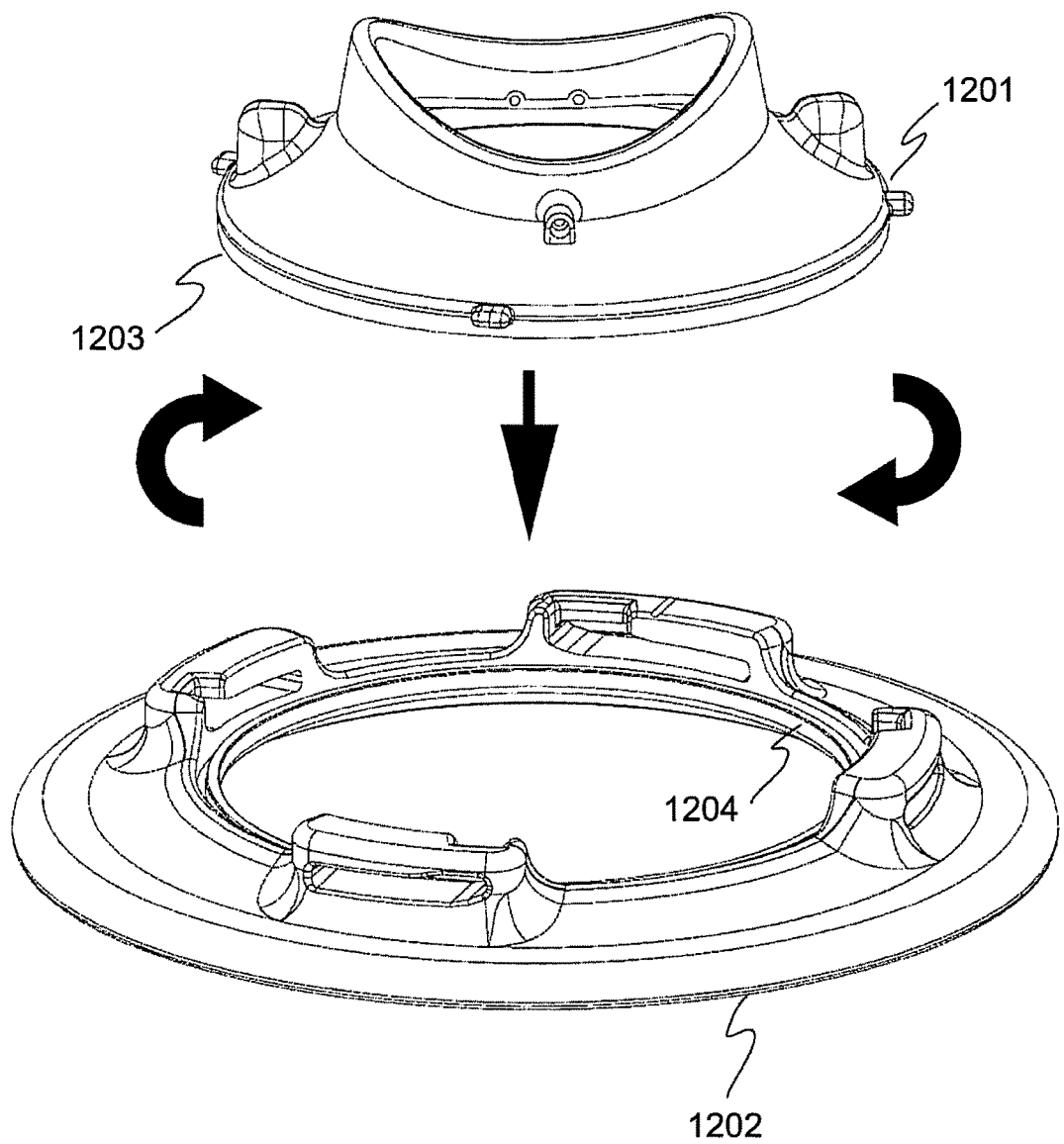
FIG. 12 illustrates another alternate embodiment of an eyepiece for an arc scanner.

FIG. 12 illustrates yet another an embodiment of an eyepiece for an arc scanner. The eyepiece consists of a mounting ring 1202 and an eye seal ring 1201. The mounting ring 1202 is attached to and is typically a permanent part of the main arc scanner assembly. As shown here the mounting ring 1202 has several attachment grooves, such as described in FIG. 10, which can accept attaching mechanisms on the eye seal ring 1201. In this embodiment, the attaching mechanisms are pushed down into the attachment grooves and then rotated into position, such as described in FIG. 10, to form a mechanical connection that seals the eye seal ring against the mounting ring to prevent water leakage. This is also known as a bayonet type connection. In the embodiment disclosed in FIG. 12, there is an additional sealing feature consisting of a groove 1203 molded as part of the eye seal ring 1201 and a matching tongue 1204 molded as part of the mounting ring 1202. When the eye seal ring 1201 is rotated into position with the mounting ring 1202, the tongue and groove form a threaded connection as described in FIG. 13 which compress as the parts are rotated into position. This is similar in sealing action to a plastic bottle with a threaded top. Since both the eye seal ring 1201 and the mounting ring 1202 are typically made from a plastic, the compliance of the plastic further helps in forming a water tight seal. The eye seal ring 1201 has a soft rubber or foam face seal (not shown here) which is designed to seal against a typical human face around the eye that is to be scanned. A sealed hygienic barrier (not shown) is formed as part of the eye seal ring 1201 and is typically located where the contoured face seal is connected to the main body of the eye seal ring 1201.

FIG. 13 shows a section side view illustrating the tongue and groove portion of the sealing method for the eyepiece of FIG. 12. FIG. 13a shows an eyepiece consisting of a mounting ring 1302 and an eye seal ring 1301 is shown in sectional view with its tongue and groove sealing system indicated by callout 1303.

FIG. 13b illustrates a close up view of tongue and groove portion of the sealing method for the eyepiece of FIG. 13a. The eyepiece mounting ring 1312 has a tongue 1314 molded into the eyepiece mounting ring 1312. The eye seal ring 1311 has a matching groove 1313 molded into the eye seal ring 1311. When the eye seal ring 1311 is rotated into position with the mounting ring 1312, the tongue 1314 and groove 1313 compress, deform as necessary and form a tight seal as the parts are rotated into position.

As described previously, the eye seal ring typically includes a soft rubber or foam contoured face seal which is designed to seal against a typical human face around the eye that is to be scanned. The contoured face seal may also be made from a foam material impregnated with, for example, mineral oil, to provide a superior sealing action against a typical human face around the eye. An alternative face sealing mechanism can also be provided by a hollow soft rubber or soft plastic ring molded into the removable eye seal ring that can be filled with water after the patient has placed their face against the eyepiece. This would be a third separate water-filled component of an arc scanner and would serve to better seal against the face around the eye for patient's with irregular facial features around the eye.

A number of variations and modifications of the inventions can be used. As will be appreciated, it would be possible to provide for some features of the inventions without providing others. For example, though the embodiments are discussed with reference to an arc scanning device, it is to be understood that the various embodiments may be used with other types of scanning devices, such as sector scanning devices.

The present invention, in various embodiments, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An ultrasonic arc scanning device, comprising:
   a chamber configured to hold a fluid;
   an eyepiece for positioning an eye of a patient relative to the chamber;
   a guide track positioned in the chamber;
   a movable transducer carriage comprising a transducer holder, wherein the transducer carriage is configured to move along a length of the guide track;
   an ultrasonic transducer engaged with the transducer holder of the transducer carriage, wherein the guide track, the transducer carriage, and the ultrasonic transducer are operable in the fluid of the chamber; and
      a magnetic tracking system, comprising a magnetic strip attached to the guide track and an encoder attached to the transducer carriage to determine a location of the transducer carriage along the length of the guide track, wherein the encoder senses a position of the transducer carriage by reading the magnetic strip positioned along the longitudinal length of the guide track, and wherein the magnetic strip has alternating north/south poles and a distance between poles known to the encoder.

2. The device of claim 1, wherein the magnetic tracking system comprises a magnetic field sensor, a sensed magnetic field being related to a position along the guide track.

3. The device of claim 1, wherein the magnetic tracking system comprises an electronic counter, the electronic counter producing a count, the count being related to a position along the guide track.

4. The device of claim 1, further comprising:
   a linear induction motor for moving the transducer carriage along the guide track, the linear induction motor comprising at least one magnet in the transducer carriage and an iron-containing core surrounded by a plurality of electric coil segments in the guide track; and
   a controller operable, at a selected point in time, to selectively energize an electric coil segment in proximity to a sensed position of the carriage.

5. The device of claim 1, further comprising:
   a linear induction motor for moving the transducer carriage along the guide track, the linear induction motor comprising at least one magnet in the transducer carriage and an iron-containing core surrounded by a plurality of electric coil segments in the guide track; and
   a controller operable, at a selected point in time, to selectively energize the ultrasonic transducer in response to a sensed position of the transducer carriage to produce a desired physical spacing of ultrasound pulses.

6. The device of claim 1, wherein at least one of a velocity and acceleration of the transducer carriage is non-uniform along the guide track.

7. The device of claim 1, wherein the magnetic tracking system is adapted to determine the location of the transducer carriage along the length of the guide track.

8. The device of claim 1, further comprising:
   a linear induction motor for moving the transducer carriage along the guide track, the linear induction motor comprising two permanent magnets in the transducer carriage and an iron-containing core surrounded by a plurality of electric coil segments in the guide track, wherein the two permanent magnets are arranged with alternating polarities.

9. The device of claim 8, wherein the two permanent magnets have a predetermined length along the length of the guide track that is approximately equal to a predetermined length of three electric coil segments along the length of the guide track.

10. An ultrasonic arc scanning device, comprising:
    a chamber configured to hold a fluid;
    an eyepiece for positioning an eye of a patient relative to the chamber;
    a guide track positioned in the chamber;
    a movable transducer carriage comprising a transducer holder, wherein the transducer carriage is configured to move along a length of the guide track;
    an ultrasonic transducer engaged with the transducer holder of the transducer carriage, wherein the guide track, the transducer carriage, and the ultrasonic transducer are operable in the fluid of the chamber; and
       an optical tracking system, comprising an optical strip attached to the guide track and an encoder attached to the transducer carriage to determine a location of the transducer carriage along the length of the guide track, wherein the encoder senses a position of the transducer carriage by reading a bar code imprinted on the optical strip positioned along the length of the guide track, and wherein the optical strip has alternating light and dark stripes and a predetermined distance between stripes known to the encoder.

11. The device of claim 10, wherein the encoder senses a position of the transducer carriage by illuminating a length of the guide track with light and sensing at least one of a refractive, diffractive, and reflective distribution of light.

12. The device of claim 11, wherein the encoder illuminates the bar code positioned along a length of the guide track, the bar code producing a unique distribution of reflected light at any position along the length of guide track.

13. The device of claim 10, further comprising:
a linear induction motor for moving the transducer carriage along the guide track, the linear induction motor comprising at least one magnet in the transducer carriage and an iron-containing core surrounded by a plurality of electric coil segments in the guide track; and
a controller operable, at a selected point in time, to selectively energize an electric coil segment in proximity to a sensed position of the transducer carriage.

14. The device of claim 10, further comprising:
a linear induction motor for moving the transducer carriage along the guide track, the linear induction motor comprising at least one magnet in the transducer carriage and an iron-containing core surrounded by a plurality of electric coil segments in the guide track; and
a controller operable, at a selected point in time, to selectively energize the ultrasonic transducer in response to a sensed position of the transducer carriage to produce a non-uniform, desired physical spacing of ultrasound pulses.

15. The device of claim 10, wherein at least one of a velocity and acceleration of the transducer carriage is non-uniform along the guide track.

16. The device of claim 10, wherein the optical positioning system is adapted to determine the location of the transducer carriage relative to the guide track with a 2-micron resolution.

17. The device of claim 10, further comprising:
a linear induction motor for moving the transducer carriage along the guide track, the linear induction motor comprising two permanent magnets in the transducer carriage and an iron-containing core surrounded by a plurality of electric coil segments in the guide track, wherein the two permanent magnets are arranged with alternating polarities.

18. The device of claim 17, wherein the two permanent magnets have a predetermined length along the length of the guide track that is approximately equal to a predetermined length of three electric coil segments along the length of the guide track.

19. The device of claim 10, wherein the encoder illuminates the bar code positioned along a length of the guide rack, and the bar code is configured to produce a unique distribution of reflected light at any position along the length of the guide track.

20. The device of claim 10, wherein the optical tracking system comprises an electronic counter, the electronic counter producing a count, the count being related to a position along the guide track.

* * * * *